United States Patent [19]

Gombrich et al.

[11] Patent Number: 4,857,716
[45] Date of Patent: Aug. 15, 1989

[54] PATIENT IDENTIFICATION AND VERIFICATION SYSTEM AND METHOD

[75] Inventors: Peter P. Gombrich; Ronald E. Zook, both of Boulder, Colo.; Max S. Hendrickson, Forest Lake, Minn.

[73] Assignee: CliniCom Incorporated, Boulder, Colo.

[21] Appl. No.: 205,527

[22] Filed: Jun. 8, 1988

Related U.S. Application Data

[63] Continuation of Ser. No. 862,278, May 12, 1986, abandoned, which is a continuation-in-part of Ser. No. 757,277, Jul. 19, 1985, abandoned.

[51] Int. Cl.$^4$ .............................................. G06K 7/10
[52] U.S. Cl. .................................... 235/462; 235/375; 235/472; 340/825.34; 379/95
[58] Field of Search ............... 235/375, 382, 462, 472, 235/435, 487; 320/35; 379/95; 340/825.34

[56] References Cited

U.S. PATENT DOCUMENTS

| | | |
|---|---|---|
| 3,439,320 | 4/1969 | Ward . |
| 3,685,723 | 8/1972 | Berler ................................... 235/472 |
| 3,715,570 | 2/1973 | Weichselbaum et al. . |
| 3,803,571 | 4/1974 | Luz . |
| 3,826,900 | 7/1974 | Moellering ........................... 235/435 |
| 3,831,006 | 8/1974 | Chaffin et al. ....................... 235/375 |
| 3,848,112 | 11/1974 | Weichselbaum et al. . |
| 3,891,980 | 6/1975 | Lewis et al. . |
| 3,898,619 | 8/1975 | Carsten et al. . |
| 4,006,397 | 2/1977 | Catotti et al. ....................... 320/35 X |
| 4,121,574 | 10/1978 | Lester . |
| 4,180,204 | 12/1979 | Koenig et al. .................. 235/487 X |
| 4,209,787 | 6/1980 | Freeny, Jr. . |
| 4,227,258 | 10/1980 | Root et al. . |
| 4,274,083 | 6/1981 | Tomoeda . |
| 4,303,910 | 12/1981 | McCann . |
| 4,337,462 | 6/1982 | Lemelson . |
| 4,359,631 | 11/1982 | Lockwood et al. . |
| 4,445,028 | 4/1984 | Huber . |
| 4,471,165 | 9/1984 | Defino et al. . |
| 4,471,345 | 9/1984 | Barrett, Jr. . |
| 4,473,884 | 9/1984 | Behl . |
| 4,476,381 | 10/1984 | Rubin . |
| 4,481,382 | 11/1984 | Villa-Real . |
| 4,483,683 | 11/1984 | Alley, Sr. . |
| 4,486,624 | 12/1984 | Puhl et al. . |
| 4,488,035 | 12/1984 | Withnall et al. . |
| 4,489,313 | 12/1984 | Pfister . |
| 4,491,725 | 1/1985 | Pritchard . |
| 4,508,935 | 4/1985 | Mastromoro . |
| 4,519,066 | 5/1985 | Barrett, Jr. et al. . |
| 4,523,087 | 6/1985 | Benton . |
| 4,528,444 | 7/1985 | Hara et al. . |
| 4,588,881 | 5/1986 | Pejas et al. . |
| 4,593,155 | 6/1986 | Hawkins . |
| 4,598,275 | 7/1986 | Ross et al. . |
| 4,625,276 | 11/1986 | Benton et al. . |
| 4,628,193 | 12/1986 | Blum ................................ 235/472 X |
| 4,634,810 | 1/1987 | Grassl et al. . |

OTHER PUBLICATIONS

Potential Use of Bar Codes to Implement Automated Dispensing Quality Assurance Programs, *Hospital Pharmacy*, vol. 20, May 1985, by Hokanson et al.

Bar Coding for Medical Device Labeling, *MD & DI*, Aug. 1983, by Richard Farb.

(List continued on next page.)

Primary Examiner—David L. Trafton
Attorney, Agent, or Firm—Merchant, Gould, Smith, Edell, Welter & Schmidt

[57] ABSTRACT

A patient identification system for relating items with patients and ensuring that an identified item corresponds to an identified patient. The patient identification system includes a computer system (42) interconnected to a plurality of remote terminals (62) by conventional telephone wiring (66,70). The patient identification system further including a portable bar code reading device (48) including a bar code wand (120), an LCD display (116) and a key pad (114). The portable bar code reading device (48) communicates via RF transmission with an RF/PLC modem (60). The bar code reading device (48) is utilized to read a patient's unique bar codes (50) on a patient's identification bracelet (52), bar codes (51) on labels (53) attached to various items in the hospital relating the item to a specific patient and bar codes (49) on item labels (47) whereby such items can be automatically correlated to a specific patient and checks performed at the computer system (42) to ensure that the item properly corresponds to the identified patient.

4 Claims, 19 Drawing Sheets

OTHER PUBLICATIONS

A Uniform Labeling System for Blood Services by Hubbell et al., *Medical Instrumentation*, vol. 15, No. 1, Jan.–Feb. 1981.

Bar Code Finds Identity as User-Input Alternative, *Systems and Software, Apr. 1985*, by Ron Schneiderman.

An Integrated Hospital Computer System, *Systems Technology*, Dec. 1978, No. 30, Stobart et al.

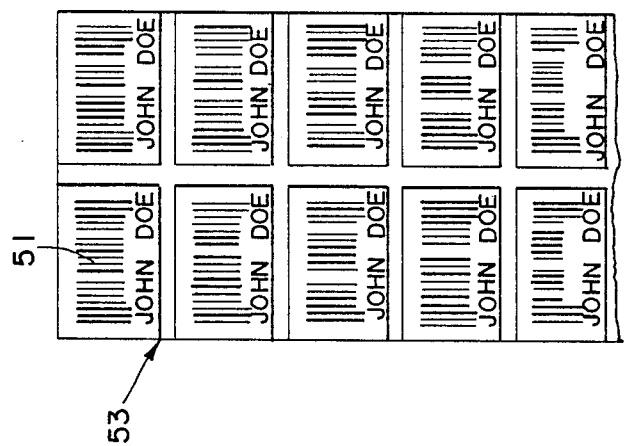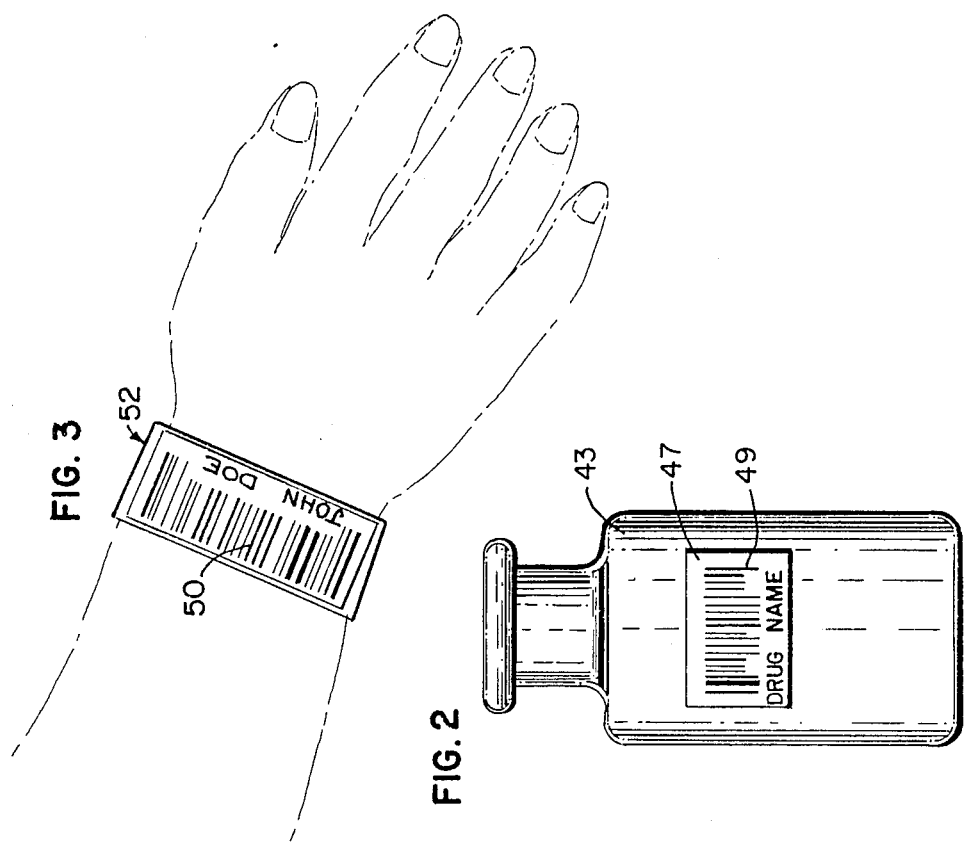

FIG. 16

| Patient 1 I.D. | Address | Allergies | History | Insurance |
| Patient 2 I.D. | Address | Allergies | History | Insurance |
| Patient N I.D. | Address | Allergies | History | Insurance |

| Item #1 | Quantity Left | Rate of Use |
| . | . | . |
| . | . | . |
| . | . | . |
| . | . | . |
| . | . | . |
| Item #2 | Quantity Left | Rate of Use |
| . | . | . |
| . | . | . |
| . | . | . |
| . | . | . |
| . | . | . |
| Item N | Quantity Left | Rate of Use |
| . | . | . |
| . | . | . |
| . | . | . |

FIG. 17

| | | | |
|---|---|---|---|
| Patient 1 I.D. | Drug 1 I.D. | Dosage | Times/Frequency |
| | Drug 2 I.D. | Dosage | Times/Frequency |
| . | . | . | . |
| . | . | . | . |
| Patient 2 I.D. | Drug 1 I.D. | Dosage | Times/Frequency |
| | Drug 2 I.D. | Dosage | Times/Frequency |
| . | . | . | . |
| . | . | . | . |
| Patient N I.D. | Drug N I.D. | Dosage | Times/Frequency |
| . | . | . | . |
| . | . | . | . |

FIG. 18

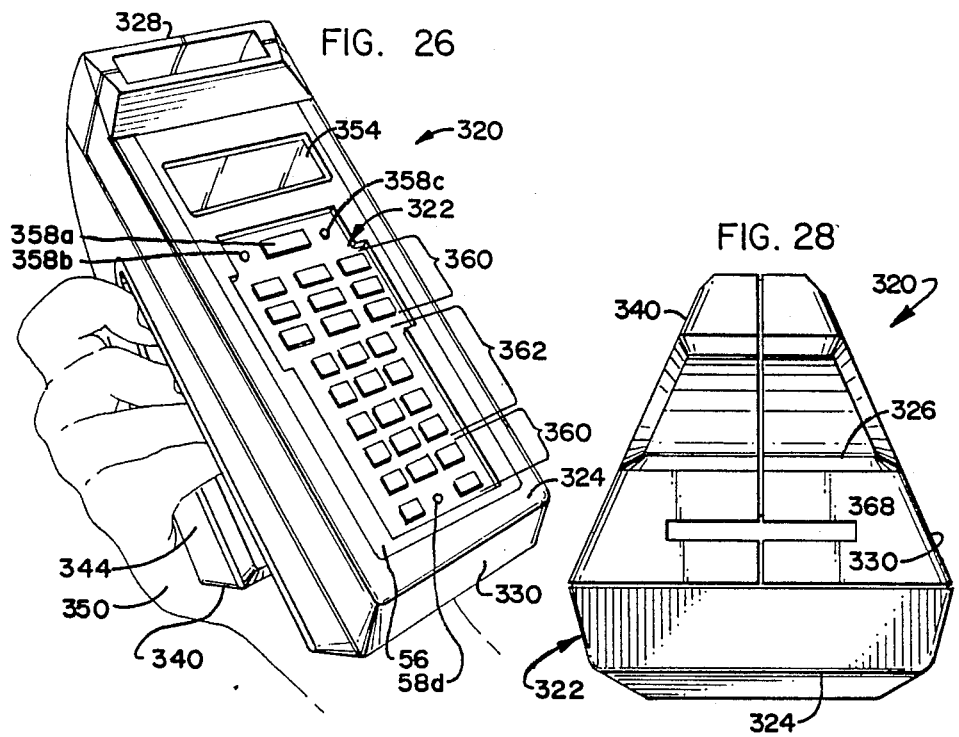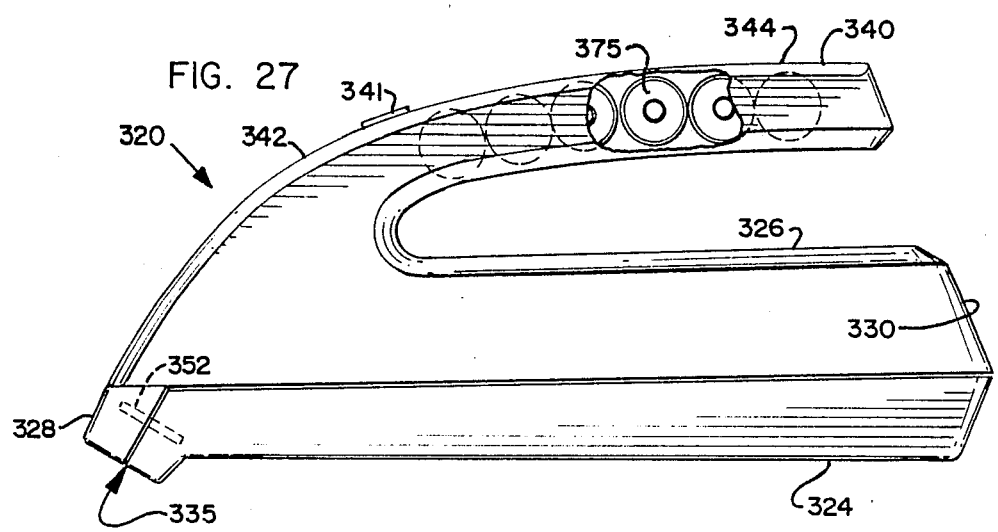

PATIENT IDENTIFICATION AND VERIFICATION SYSTEM AND METHOD

This is a continuation of application Ser. No. 862,278 filed May 12, 1986 which is a continuation-in-part of Ser. No. 757,277 filed July 19, 1985; both are abandoned.

BACKGROUND OF THE INVENTION

The present invention relates to a system and method for patient identification and clinical care verification. More particularly, the present invention relates to a patient identification system and method providing for accurate identification of a patient and for relating items to a patient and ensuring that patient specific items do properly correspond to a patient, thereby providing for accurate medical treatment, billing and inventory and cost control.

Medical institutions are faced with a competitive environment in which they must improve profitability and yet simultaneously improve patient care. There are several factors which contribute to the ever increasing costs of hospital care. For example, there is an ever increasing amount of paperwork required by nurses, pharmacists and laboratory personnel. In addition, inaccurate recording of drugs, supplies and tests involved in patient care results in decreasing revenues by a failure to fully capture billing opportunities of these actual costs. Inadequate management also results in a failure to provide an accurate report of all costs involved in treating a particular illness.

In most hospitals and clinical laboratories, a bracelet device containing the patient's name is permanently affixed around the arm of an incoming patient in order to identify the patient during his or her entire stay. Despite this, numerous situations arise which result in errors in patient identification.

For example, when a blood sample is taken from a patient, the blood sample must be identified by the name on the patient's bracelet In transferring the patient's name a nurse or technician may miscopy the name or may rely on memory or a different data source, rather than actually reading the patient's bracelet.

Moreover, the lack of accurate and rapid transfer of patient information often reduces the accuracy and/or effectiveness of drug administration and patient care, thereby increasing the duration of hospital stay.

In addition, hospitals and other institutions must continuously strive to provide quality patient care. Medical errors, where the wrong patient receives the wrong drug at the wrong time, in the wrong dosage or even the wrong surgery, are a significant problem for all health care facilities. Many prescription drugs and injections are identified merely by slips of paper on which the patient's name and identification number have been handwritten by a nurse or technician who is to administer the treatment. For a variety of reasons, such as the transfer of patients to different beds and errors in marking the slips of paper, a patient may be given an incorrect treatment.

Further, as health care facilities continue to decrease the number of staff personnel as a cost cutting measure, the possibility of personnel errors will most likely increase.

The present invention offers a system which solves or at least reduces the impact of the above-identified problems and other problems associated with health care facilities.

SUMMARY OF THE INVENTION

The present invention relates to a system for patient identification comprising a programmed general purpose computer means for processing and storing patient data. Input devices are operatively interconnected with the computer means for input of patient data into the computer. A first identification device is adapted for attachment to a patient for identification of the patient and includes a patient-unique code. A plurality of second identification devices are provided for relating various items to a particular patient, the second identification devices including a patient-unique code different from that of the first identification device so as to differentiate first and second identification devices from each other. The input means includes a portable terminal having a bar code reader for scanning the code of the first identification device to identify the patient and for scanning the code of the second identification devices. The portable terminal further includes an RF transceiver for transmitting bar code data representative of the codes scanned by the bar code reader and for receiving data. Modem means interconnected to the computer by, in part, a telephone line is adapted for receipt of the RF signal and for transmitting data to the computer via the telephone line. A plurality of terminals are located remotely from the computer at various locations and are interconnected to the computer at least in part by telephone lines for input and output of patient data to and from the computer.

One object of the present invention is to provide a patient identification system for identifying patients.

Yet another object of the present invention is to provide a patient identification system for relating items to a patient.

Another object of the present invention is to provide for identification of certain items which are patient specific, such as drugs, blood test samples, IV's, surgical procedures, etc. and to provide a cross-check to ensure that the identified item properly corresponds to an identified patient. The present invention not only provides this verification function, but provides a full audit trail of all transactions concerning patient therapy, the audit trail including staff ID, date, time flagging or marking, etc.

Still another object of the present invention is to provide for recall and review of patient information in various presentation formats at display terminals and at printer devices.

Yet another object of one embodiment of the present invention is to provide for limited access to the system and provide for identification of the person and/or department entering data respecting a patient and/or items.

An object of one embodiment of the present invention is to provide automatic billing and/or inventory control. Cost capture is provided at consumption point which is not possible with current systems.

Yet another object of one embodiment of the present invention is to provide improved communications using existing transmission paths. In particular, one embodiment uses existing telephone wiring. This eliminates the substantial cost of wiring installation required by other conventional means.

It is an object of the present invention to provide more reliable and safe treatment of patients.

It is an object of one embodiment of the present invention to provide an alert if a particular drug administration is overdue and/or improper. In one embodiment, the overdue drug alert occurs both at a nurses' terminal and at a portable bar code reading device when the nurse scans her identification bar code.

It is yet another object of the present invention to provide for the coordination and collection of data.

It is an object of one embodiment of the present invention to provide a bed-side electronic patient file for recording and recall/review of previous vital signs, drugs administered, etc.

It is an object of one embodiment of the present invention to provide for electronic generation of a medical administration record (MAR), nurses' assignment sheets, graphic presentations of vital signs versus drugs, etc. In addition, the present invention provides for an automatic source of administrative reports required by industry, thus saving staff time for clinical therapy instead of paperwork.

It is an object of one embodiment of the present invention to utilize a radio frequency bar code reader device with liquid crystal display and key pad for input to a computer system of patient identification information and item identification information so as to enable a correlation thereof. Moreover, the bar code reader device includes memory files for maintaining a record for recall and review of patient vital signs and the times PRN or other controlled drugs were administered for pain or the like.

It is an object of yet another embodiment of the present invention to provide an apparatus in each patient's room for automatically providing the bar code reader device with a unique address whenever interconnected thereto, whereby bar code reader devices can be interchanged between rooms.

It is an object of one embodiment of the present invention to provide a relatively inexpensive system which makes substantial use of existing wiring and existing technology. In particular, one embodiment of the present invention uses data over voice (DOV) transmission on existing telephone lines.

Additional objects of yet other embodiments of the present invention are to provide a system which is very easy to use; will reduce the amount of administrative paperwork such as charting and will decrease the amount of time hospital staff spend charting their activities.

Still another object of one embodiment of the present invention is to monitor a nurse's time with the patient and maintain a chronology of patient events such as when a patient is moved to another room, drugs are administered, a patient has lab tests conducted, a patient checks out of the hospital, etc. whereby a time audit can be performed on the hospital's patient activities.

It is an object of yet another embodiment to provide for narcotics inventory control.

Yet another objective of on embodiment of the present invention is to provide a data base management function.

Still another objective of one embodiment of the present invention is to provide a system and method for determining the identification and location of personnel including patients and staff members, and miscellaneous items. For example, in the case of a patient, radio frequency (RF) transmitter means is worn on the body of the patient for transmitting an RF signal including unique patient identifier information. A plurality of spaced apart RF receiver means is provided for receiving the RF signal transmitted from the RF transmitter means. The RF receiver means includes fixed position RF receiver means and portable RF receiver means, contained in portable handheld patient terminals, the portable handheld patient terminals including RF transmitter means for transmitting an RF signal. The RF receiver means includes interface means for retransmitting the unique patient identifier information over electrical wiring interconnecting the RF receiver means to central computer means. The central computer means receives the unique patient identifier information transmitted by the RF receiver means and including program means for determining patient location based on the unique patient identifier information received. A plurality of terminal means are interconnected to the central computer means for displaying the patient location upon inquiry by a user. This embodiment is particularly suited for health care institutions and more particularly nursing homes and mental institutions wherein the patients are very ambulatory and are not always cognizant of their actions.

It is an objective of yet another embodiment of the invention to provide a programmable, addressable RF transmitter to be fitted onto a disposable bracelet being worn by a patient. The RF transmitter, if its supporting electronics, and power supply are encapsulated within a media allowing for sterilization and cleaning so the RF transmitter can be used. The RF transmitter is reprogrammable such that it can be reused and programmed t transmit unique patient identifier information. The power supply is a battery with a substantially long life thereby enabling the RF transmitter to be used a number of times.

In yet another embodiment of the present invention, fixed position and portable RF receiver units are utilized. The fixed position RF receiver units are located at predetermined locations throughout the health care facility. The portable RF receiver units are mounted in portable handheld patient terminals which also include an RF transmitter for retransmission of the RF signal received from the patient worn transmitter to a fixed position RF receiver unit.

Another objective of one embodiment of the present invention is to provide fixed position RF receiver units which are hardwired to a central computer system by existing telephone wiring or twisted pair wiring and includes data over voice (DOV) modems for transmission of the unique patient identifier information over the telephone wire or RS232 interface means for transmission on the twisted pair wiring. A central computer system will be programmed to determine a patient's location based on the information received, and will display the information when so requested by a user at a terminal interconnected to the computer system.

Yet another object of the present invention is the provision of a portable handheld terminal providing wireless communication by use of an electromagnetic transceiver to a base station transceiver unit. The base station being interconnected to a host central computer system so as to provide real time or near real time communication system so as to provide real time or near real time communication between the portable handheld terminal and the host central computer system.

Still another object of the present invention is to provide a portable handheld patient terminal including optical bar code reader which is easy to hold during use. The portable handheld patient terminal includes a housing having first and second spaced apart, opposing major surfaces extending generally along a longitudinal axis of the housing between first and second end portions of the housing. Keyboard means is disposed on the first opposing surface for entering data. Display means is disposed on the first opposing surface for displaying data. Optical sensor means is disposed approximate the first end portion of the housing for sensing bar code indicia. Control means is contained in the housing and operatively interconnected to the keyboard means, display means, and optical sensor means for controlling the operation of the keyboard means, the display means, and the optical sensor means. Elongated handle means is interconnected to the housing and extends longitudinally along the second surface, the elongated handle means being spaced from the second surface along a portion thereof, whereby the handle means can be grasped by a user of the portable handheld patient terminal.

Yet another objective of the present invention is to provide a portable handheld patient terminal with a bar code reader which is self-scanning. A binary imaging sensor is provided which enables the bar code reader to self-scan the bar code indicia in both the X and Y directions. The bar code reader does not have to be moved relative to the bar code in order to read the bar code indicia. The user simply positions the binary imaging sensor over the bar code to be read and activates the sensor which takes a digital "picture" of the bar code. The digital "picture" is then processed by appropriate digital processing techniques. In addition, contact between the bar code reader and the bar code is not required. The present invention is particularly useful for reading bar codes on curved surfaces as well as flat surfaces. In addition, a bar code reader of the portable handheld patient terminal of the present invention can be used to read characters as well as bar codes.

One object of the present invention is to provide a portable handheld patient terminal providing the main data collection component of the patient identification system. In a hospital setting, it is ideally located in every patient room along with a base unit. In long term health care facilities such as nursing homes and mental health care facilities, the portable handheld patient terminal is kept at a nursing station and then carried with the nurse or other staff member as they make their rounds administering medications, taking vital signs, etc. In this particular application, the portable handheld patient terminal will have additional memory to allow storage of data relating to several patients. The data is then subsequently transmitted via an RF data communication link provided by a conveniently located base station having a transceiver function and thence from the base station over telephone wires by data over voice (DOV) techniques to a central computer system. The portable handheld patient terminal provides a means of data entry by means of a bar code reader, keypad, and a port for connection to an external vital signs measurement system. Communications is a radio frequency (RF) linked to the base unit or a direct link to a nurses' terminal via a communications port. Interaction with the user is provided by liquid crystal display (LCD), a keypad, an audio alarm, and light emitting diode (LED) indicators. The portable handheld patient terminal is preferably operated by a rechargeable battery. The base unit will provide communications between the portable handheld patient terminal via the RF link and the central computer system via a telephone link using data over voice (DOV) technology or a twisted pair wire link using existing pairs of wires or newly installed wire. In addition, the base unit might also utilize the existing AC wiring for power line carrier (PLC) communication. The base unit will include a means of communications through a port to the portable handheld patient terminal when the terminal is inserted into the base. Also included is a battery charger circuit for the portable handheld patient terminal when it is not in use, such that the rechargeable battery supply can be recharged. The base unit is ideally stationary such as being mounted on a wall and holds the portable handheld patient terminal when not in use.

The present invention, in addition to the above features and others, provides the following advantages over existing system, (1) patient identification, (2) cost capture, (3) reduction in nursing and administrative time, and (4) immediate data capture and positive identification and verification of all therapy provided to the patient.

These and various other advantages and features of novelty which characterize the invention are pointed out with particularity in the claims annexed hereto and forming a part hereof. However, for a better understanding of the invention, its advantages and objects attained by its use, reference should be had to the drawings which form a further part hereof, and to the accompanying descriptive matter, in which there is illustrated and described a preferred embodiment of the invention.

BRIEF DESCRIPTION OF THE DRAWINGS

FIG. 21–35 have been added to FIGS. 1–20 of the parent application, of which this application is a continuation-in-part.

In the drawings, in which like reference numerals and letters indicate corresponding parts throughout the several views.

FIG. 2 is a diagrammatic view of a drug vial with an item bar code identifier thereon;

FIG. 3 is a diagrammatic view of a patient identification bracelet with a patient identifier bar code thereon;

FIG. 4 is a diagrammatic view of a sheet of labels with patient identification bar code identifiers thereon;

FIG. 16 is a diagrammatic illustration of an embodiment of a patient information data file;

FIG. 17 is a diagrammatic illustration of an embodiment of a patient/drug data file;

FIG. 18 is a diagrammatic illustration of an embodiment of an inventory data file;

FIG. 21 is a block diagram of an alternate embodiment of the present invention including a patient identification and location system;

FIG. 22 is a block diagram of an embodiment of an RF transmitter unit including RF transmitter, control circuitry, and power supply sealed in a protective media;

FIG. 23 is a block diagram of an embodiment of an RF receiver unit;

FIG. 24 is a functional flow diagram of an embodiment of a patient identification and location method in accordance with the principles of the present invention;

FIG. 25 is a block diagram of an embodiment of a portable handheld patient terminal in accordance with the principles of the present invention;

FIG. 26 is a perspective view of an alternate embodiment of a portable handheld patient terminal including optical bar code reader;

FIG. 27 is a side elevational view of the portable handheld patient terminal shown in FIG. 26;

FIG. 28 is a back end elevational view of the portable handheld patient terminal shown in FIG. 26;

FIG. 29 is a block diagram of an embodiment of a portable handheld patient terminal shown in FIG. 26;

FIG. 30 is a perspective view of the portable handheld patient terminal shown in FIG. 26 mounted in a base station;

FIG. 31 is a side view of the base station and its respective portable handheld patient terminal mounted thereon;

FIG. 32 is a block diagram of one embodiment of the base station;

FIG. 33 is a block diagram of one embodiment illustrating use by the recharging circuitry of a power supply temperature sensor;

FIG. 34 is a block diagram of one embodiment of the recharging procedure; and

FIG. 35 is an embodiment of a keyboard arrangement of the portable handheld patient terminal.

DETAILED DESCRIPTION OF THE PREFERRED EMBODIMENT

While the detailed description is provided in terms of a hospital environment, it will be appreciated that the present invention has application and utility to a variety of patient care facilities wherein patient identification and relating items including such disposable items as drugs, supplies, etc. to a particular patient is desirable and important for proper care, administration, inventory control and billing.

Figure 1:
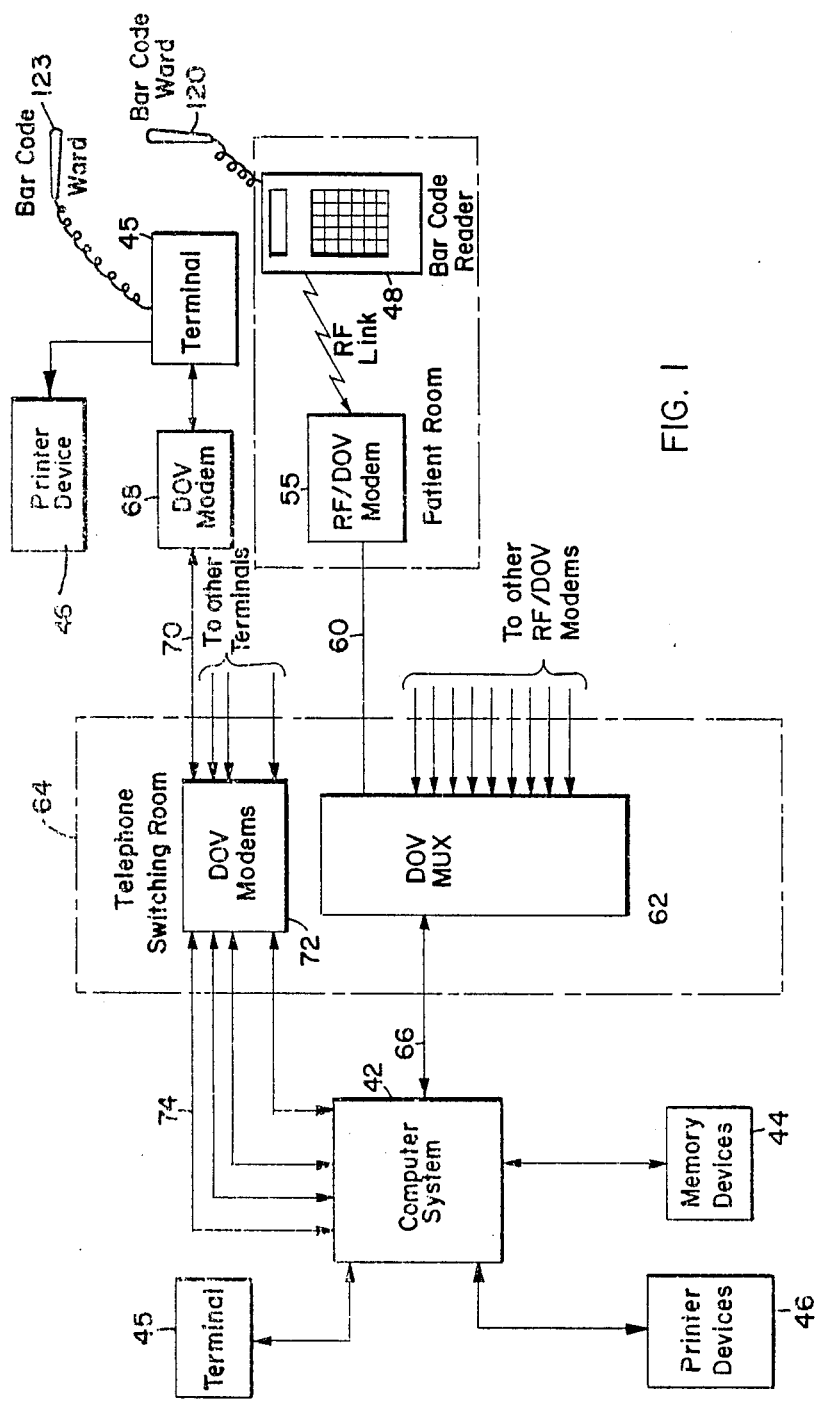
FIG. 1 is a block diagram of an embodiment of a patient identification system in accordance with the principles of the present invention.

Referring now to the drawings, there is illustrated in FIG. 1 an embodiment of a patient identification system generally referred to by the reference numeral 40 in accordance with the principles of the present invention. As illustrated, the patient identification system 40 include a programmed general purpose computer system 42; for example, a super microcomputer with 2 Mbytes of random access memory. The computer system 42 includes appropriate memory devices 44 such as floppy diskette drives, hard disk drives, streaming tape backup, etc; for example, a 145 Mbyte 8" disk drive might be used. In addition, the computer system 42 includes appropriate printer devices 46 for printout of information such as patient identification bracelets; patient identification labels, item identification labels for drugs, blood test samples, surgical supplies, IV solutions, etc.; generation of medical records (MAR); billing statements, etc. Certain ones of the printer devices are preferably portable, hand-held printers capable of printing alpha/numerics and bar codes. In addition, the computer system 42 will include terminals 45 including a keyboard and a display for input of data to and output of data from the computer system 42. The terminals 45 and the printer devices 46 might be located locally and at remote locations, as required; for example, in the pharmacy, in the laboratory, in the supply room, in X-ray, in radiology, in the billing department, at the nurses' stations, etc.

In a typical hospital application, hospital items including drugs, general supplies, etc. will include a label 47 with an item identification bar code 49 attached thereto. Diagrammatically illustrated in FIG. 2 is a drug vial 43 with such a label and bar code. Custom made items such as special medications, tests, IV's, etc. made for a specific patient will preferably have a label with a custom made item identification bar code attached at the time those items are made. Patients will have a patient identification bar code 50 appearing on their identification bracelet 52, as diagrammatically illustrated in FIG. 3, along with the patient's name. In addition, a patient identification bar code 51 will appear on the patient's medical chart and will preferably also appear on a supply of labels 53 in the patient's file. Illustrated in FIG. 4 is a sheet of such adhesive labels 53 which might be placed in a patient's medical file and then peeled off and applied to various items so as to relate those items to the patient, as required. The bar code format comprises a series of printed bars of various widths and spacing, preferably in accordance with a standard bar code system, such as the National Drug Code (NDC), Health Industry Bar Code (HIBC), Universal Product Code (UPC), Health Care Provider Application (HCPA), etc.

Typically, each patient room will be provided with a portable bar code reading device 48 which will be used to read the patient and item identification bar codes. However, it will be appreciated that there might be many other ones of the bar code reading devices 48 located throughout the hospital, and indeed, each nurse and/or patient's bed might have one of the bar code reading devices 48. Moreover, nonportable bar code reading devices might be used in some areas of the hospital where portability is not necessary or desirable. The patient identification bar codes 50 on the patient's identification bracelet 52 will specifically identify the patient, while the patient identification bar codes 51 on the labels 53 will be used to relate the various items to which they are attached to a particular patient. Preferably, the bar codes 50 on the patient's identification bracelet 52 will not be the same as the bar code 51 on the labels 53, such that the source of a bar code can be identified as being a patient or as being an item relating to that patient.

In the embodiment illustrated in FIG. 1, data representative of the bar code identifier scanned by the bar code reader device 48 is transmitted as a radio frequency (RF) signal to an RF/data over voice (DOV) modem transceiver 55 located in the patient's room where the bar code reader device 48 is located. As diagrammatically illustrated in FIG. 5, the RF/DOV modem transceiver 55 includes an RF modem 56 interconnected to a DOV modem 57 by a microprocessor 58 which serves as a protocol handler enabling communication between the modems 56, 57. The RF modem 56 provides for transmission and reception of RF signals to and from the bar code reading device 48 and the DOV modem 57 provides for transmission and reception of signals via in place, existing telephone wiring such as twisted pair or 4-wire to and from the computer system 42 using DOV technology. The RF/DOV modem transceivers 55 in the various hospital rooms are interconnected by separate telephone wires 60 such as twisted pair or 4-wire to a DOV modem/multiplexer (MUX) 62 located in the hospital's telephone switching room 64. The DOV/MUX 62 is interconnected to a single port of the computer system 42, which is preferably a network port such as an ETHERNET port, by a hardwired connection 66. Conventional DOV technology enables transmission of data at rates of up to 19.2 kilobits per second. In yet other embodiments of the present invention, limited distance modems might be used in conjunction with dedicated telephone wiring such as twisted pair or 4-wire and appropriate devices such as RS-422 drivers. The DOV/MUX 62 might transmit data to and from the computer system 42 at the rate of 9600 baud or higher.

The terminals 45 located remotely of the computer system 42 are interconnected to a DOV modem 68 which transmits data to and from the computer system 42 over existing twisted pair telephone wires 70 to DOV modem 72 located in the telephone switching room 64. The DOV modems 72 are interconnected by separate hardwired interconnects 74 to serial RS 232 ports of the computer system 42.

The embodiment of the invention illustrated in FIG. 1 enables communication from the remotely located terminals 45 and the portable bar code reader devices 48 to occur over conventional twisted pair telephone wires, thereby reducing costs and facilitating installation. It will be appreciated that various embodiments of the patient identification system might be utilized in keeping with the principles of the present invention. For example, the portable bar code reading device 48 might utilize infrared (IR) transmission/reception in place of RF transmission. In yet another embodiment, the RF/DOV modem transceiver 55 might be replaced by an RF/Power Line Carrier (PLC) modem transceiver which enables communication via AC power lines to an intermediate location, such as a nurses' station, where a PLC/DOV modem might transmit the signal to the computer system 42 by telephone wires.

Figure 6:
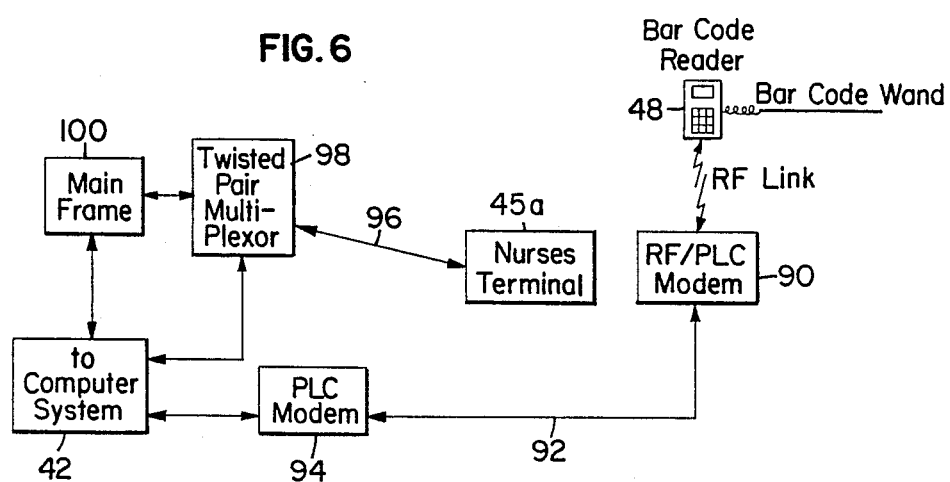
FIG. 6 is a block diagram of an alternate embodiment of a patient identification system in accordance with the principles of the present invention.
Figure 7:
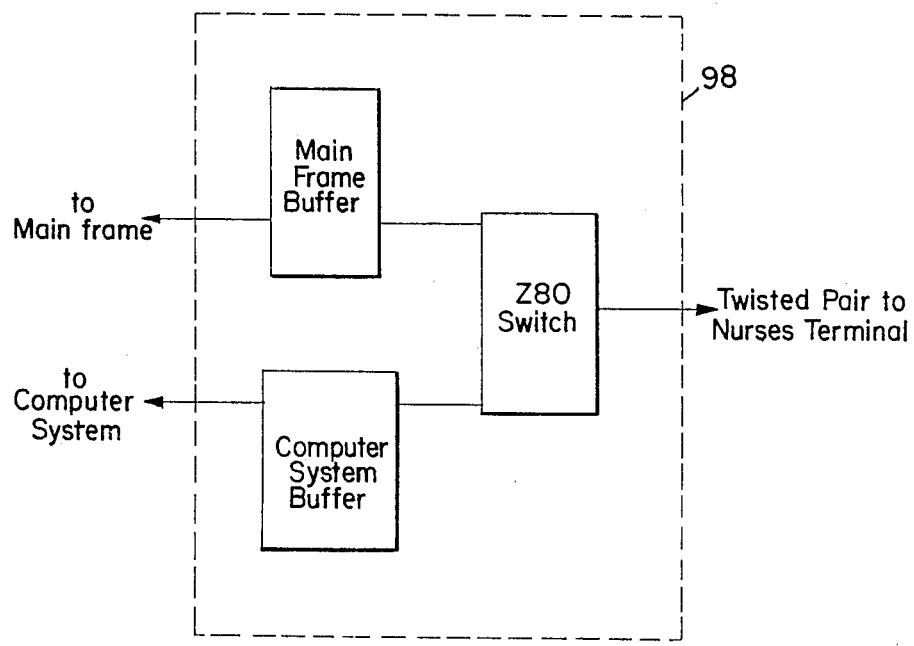
FIG. 7 is a block diagram of an embodiment of the twisted pair multiplexer illustrated in FIG. 5.
Figure 8:
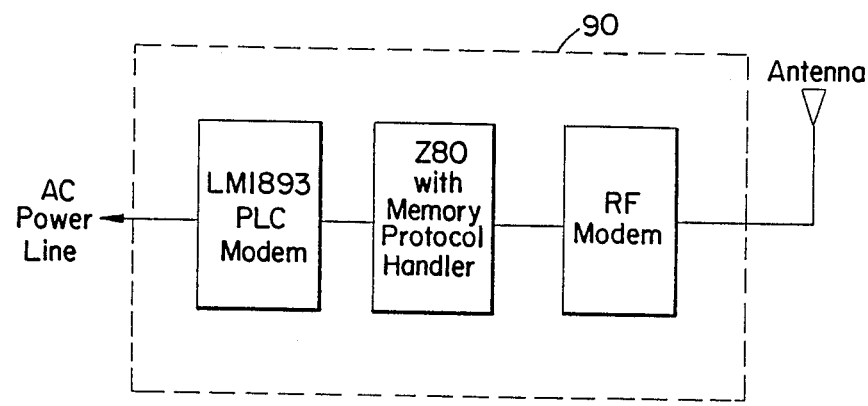
FIG. 8 is a block diagram of an embodiment of the RF/PLC modem illustrated in FIG. 5.
Figure 9:
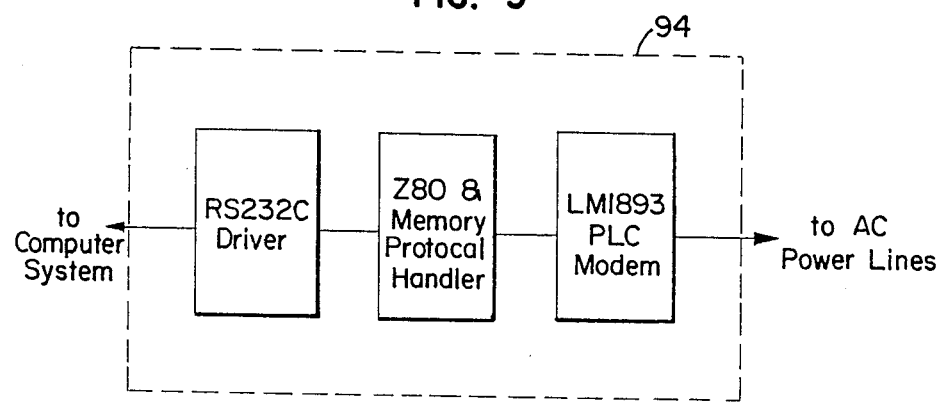
FIG. 9 is a block diagram of an embodiment of the PLC modem illustrated in FIG. 5.

Illustrated in FIGS. 6 through 9 is an alternate embodiment of the present invention wherein communications occur mostly over existing AC power lines and twisted pair wire. The bar code reader device 48 in this embodiment communicates with an RF/power line carrier (RF/PLC) modem 90, an embodiment of which is illustrated in FIG. 8. The RF/PLC modem 90 transmits data on existing AC power lines 92 to a power line carrier (PLC) modem 94, an embodiment of which is illustrated in FIG. 9. As illustrated in FIG. 6, the nurses' terminals 45a are interconnected by twisted pair wiring 96 to a twisted pair multiplexer 98, an embodiment of which is illustrated in FIG. 7. The twisted pair wiring 96 provides for faster communication than the AC power lines. The twisted pair multiplexer 98 provides communication with the computer system 42 and/or with an existing hospital mainframe computer 100. The power line carrier (PLC) is a somewhat noisy medium which will necessitate a robust protocol. Data bit errors encountered are usually burst errors where more than one bit is affected. This embodiment will preferably use a protocol involving the first three layers of the international standard organization standard. The PLC protocol will include individual addressing of devices, data field length and data similar to high level data link control (HDLC), but unlike HDLC, the protocol will be asynchronous. Error detection will be via a sixteen bit CRC with the message being retransmitted when an error is detected. Since multiple devices can be on the power lines at the same time, a collision detect multiple access (CSMA/CD) scheme with random backoff will be used. Non-coherent frequency shift keying (FSK) is preferably the modulation used, with 160 KHz being the operating frequency. The protocol to the computer system will be standard ASCII with one bit parity error detection. The PLC modem 94 will include a microprocessor such as the Z80 with a two Kbyte memory for handling the communications protocol between the AC power lines and the computer system. The LM1893 IC from National Semiconductor is used in the interface to the AC power lines and the RS232 driver is used in the interface to the computer system. The RF/PLC modem 90 will be located near the nurses' station and will relay information between the bar code reading device 48 and the PLC modem 94 near the computer system.

A frequent error in UHF transmission is multipathing. This is caused by the RF signal bouncing off objects and arriving at the receiver as two out of phase signals. Multipathing could occur in the present invention because of a nurse moving a medication cart around the room, etc. Accordingly, the same protocol selected for the PLC medium will be used to detect errors and retransmit data. The twisted pair multiplexer 98 enables the mainframe computer 100 and the computer system 42 to communicate with terminals at various locations. Preferably, in the event of a failure at the twisted pair multiplexer 98 or the computer system 42, normal communications are automatically set up between the mainframe 100 and the nurses' terminal 45a. The twisted pair multiplexer 98 will preferably not affect protocols of the mainframe 100 or the computer system 42. Data passed will be time division multiplexed and will reside in the twisted pair multiplexer's buffering memory during simultaneous transmissions.

It will be appreciated that the computer system 42 of the preferred embodiment, although not illustrated in FIG. 1, might also be interconnected to an existing hospital mainframe computer with proper protocol conversion. If there is no direct interconnection, or if communication to the hospital mainframe computer is not otherwise provided, data can be downloaded into the mainframe computer by manually transferring data storage media, such as diskettes, magnetic tape, etc. from the computer system 42 to the mainframe system 100.

Figure 10:
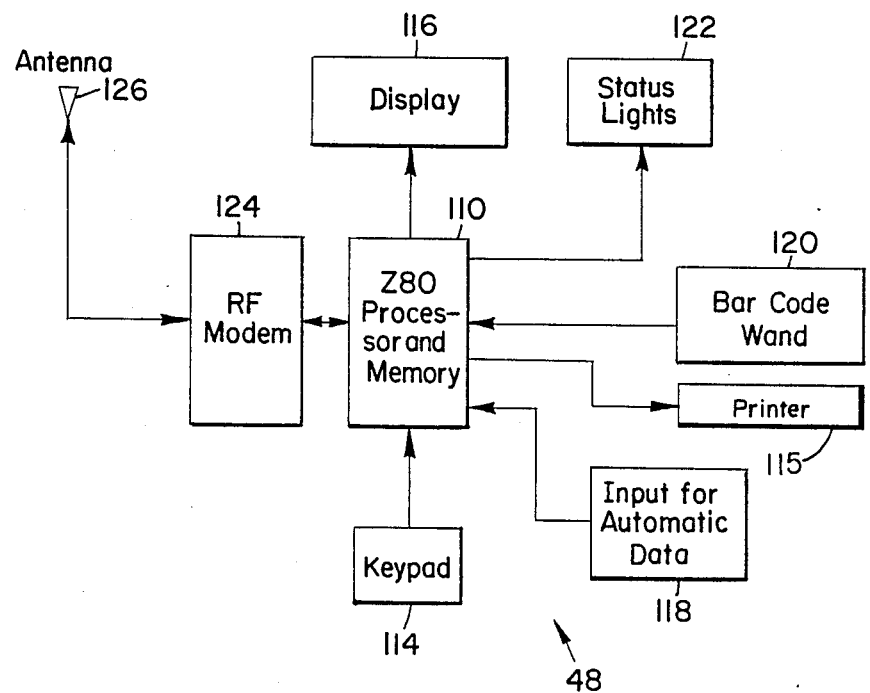
FIG. 10 is a block diagram of an embodiment of a portable bar code reader device in accordance with the principles of the present invention.
Figure 11:
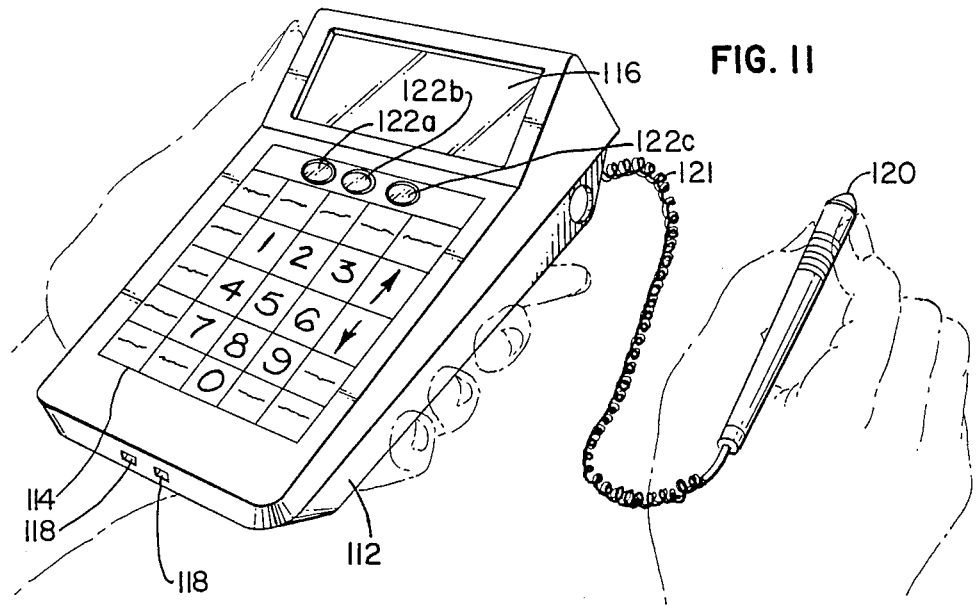
FIG. 11 is a perspective view of an embodiment of a portable bar code reading device in accordance with the principles of the present invention.
Figure 12:
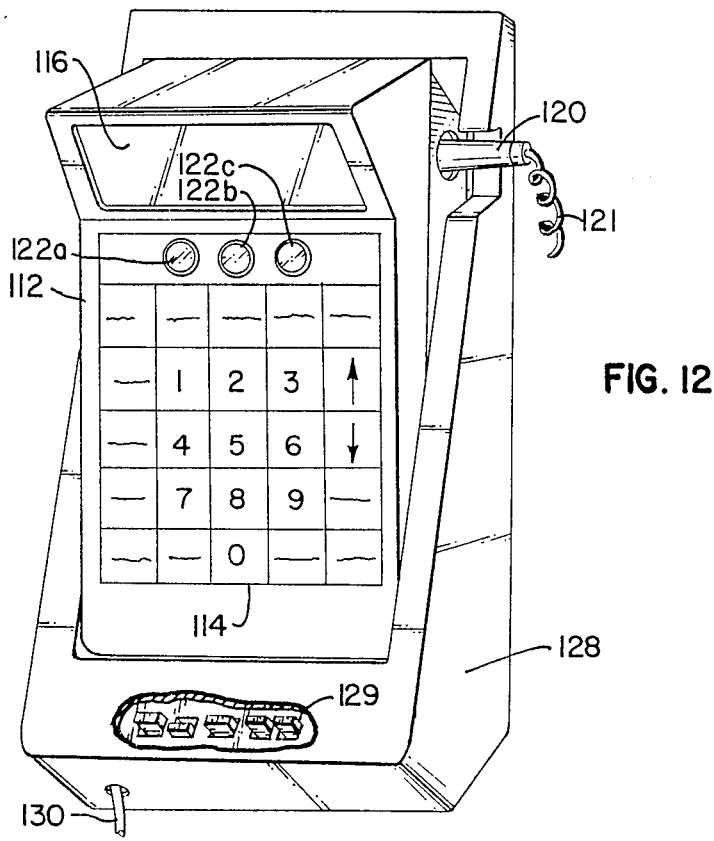
FIG. 12 is a perspective view of the embodiment of the bar code reading device illustrated in FIG. 10 with the bar code reading device mounted in a wall-mounted rechargable housing unit.

As illustrated in FIGS. 10 through 12, an embodiment of the bar code reading device 48 might include a programmed microprocessor 110, such as a Z80 and its associated memory and real time clock mounted in a hand held housing 112. The bar code reading device will preferably use low voltage battery power for portability and to prevent shocks to a patient. In addition, a key pad 114 is provided for entry of data and commands. An LCD display 116 will be provided for displaying information and status. Input/output channels 118 might be present for input of data directly into the microprocessor 110 from such items as a temperature sensor, pulse sensor, blood pressure sensor, respiration rate sensor, etc. and output of data to such items as a portable alpha/numeric bar code label printer 115 for printing bar code labels in the patient's room at bedside. The bar code reading device 48 includes a wand device 120 interconnected by a cord 121, the wand device 120 including a light emitting source for illuminating a bar code and an optical detector for reading the resulting reflections from the bars of the bar code. The wand device 120 preferably uses a light emitting diode (LED) as a light emitting source, although an infrared (IR) or laser light source can also be used. In an alternate embodiment, the wand device 120 might include an optical imaging capability utilizing charge coupled devices (CCD's) or optic random access memory (RAM). The remote terminals 45 might also be interconnected to a similar wand device 123 for reading bar codes at the terminals. The bar code reading device 48 is preferably provided with status lights 122 for providing a visual confirmation of proper correlation between an item, such as an IV solution, and the patient. In FIGS. 11 and 12, three such status lights 122a,b,c are shown, the status lights being red, amber and green. The bar code reading device 48 will preferably include an RF modem transceiver 124 and associated antenna 126 for transmission/reception of an RF signal. In yet other embodiments, the bar code reading device 48 might include an infrared transmitter/receiver arrangement to enable transmission/reception of data as an infrared signal. The bar code reading device 48 might be mounted in a wall mounted recharging unit 128 when not in use to enable recharging of batteries which might be used to power the bar code reading device 48. The recharging unit 128 is interconnected to the AC power supply by an electrical cord 130. The RF/DOV modem 55 might be a part of the recharging unit 128. As illustrated, the bar code reading device 48 is preferably a hand held unit to facilitate portability and ease of use. Moreover, although not shown, the bar code reading device 48 might include a clip or other suitable device enabling attachment to a patient's chart.

Each of the recharging units 128 will preferably have a unique address which can be manually set by a dip switch 129 or the like mounted inside the housing of the recharging unit 128 so that data transmitted to and from the portable bar code reader 48 will be addressed for a particular recharging unit 128. Moreover, the recharging unit 128 will preferably only communicate with a bar code reading device 48 having a corresponding address and will preferably include circuitry for automatically coding the portable bar code reading device 48 with the corresponding address when the portable bar code reading device 48 is mounted in the recharging unit 128 whereby portable bar code reading devices 48 can be moved from one room to another without interfering with the other portable bar code reading devices, since a bar code reading device will only communicate with a recharging unit with a corresponding address.

In the embodiment shown, the key pad 114 includes a ten key arrangement for entry of numerals and the following special function keys:

| KEY | DESCRIPTION |
| --- | --- |
| On/Off | Switches the bar code reading device on and off |
| BLD PSR | Enables input of blood pressure. |
| HRT RATE | Enables input of heart/pulse rate. |
| TEMP | Enables input of temperature. |
| DOS | Enables input of drug dosages. |
| PRT | Enables printing of identification labels. |
| CLR | Enables an entry to be cleared. |
| READ | Enables input of bar code information from the wand device. |
| HOLD | Indicates patient data files are not to be updated; for example, administration of a drug did not occur. |
| CNCL | Enables a series of entries to be cancelled. |
| SEND | Enables the transmission of data from the bar code reading device to the computer system. |
| CLK | Enables a readout of the time at the LCD display. |

It will be appreciated that numerous combinations and arrangements of special function keys might be utilized in keeping with the principles of the present invention.

Figure 13:
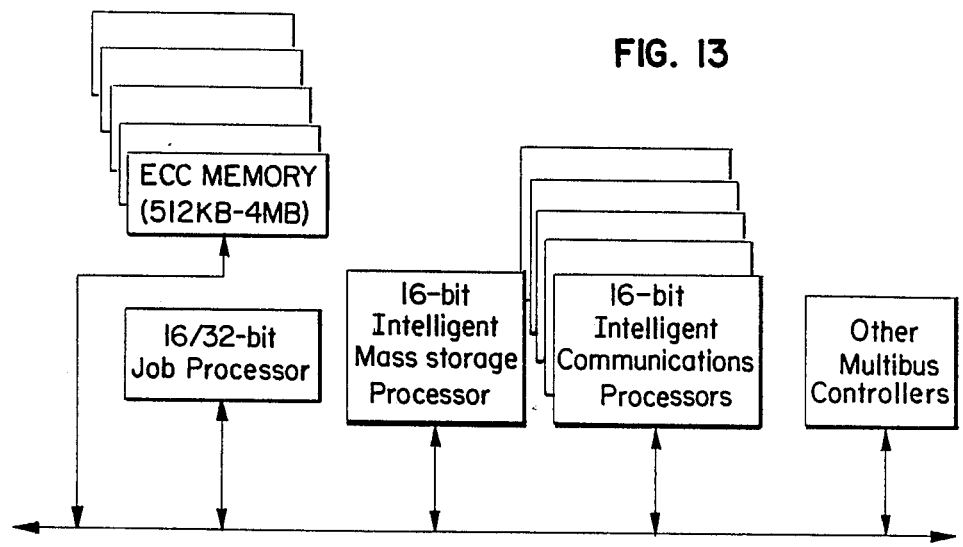
FIG. 13 is a block diagram of an embodiment of microcomputer architecture which might be utilized in accordance with the principles of the present invention.
Figure 14:
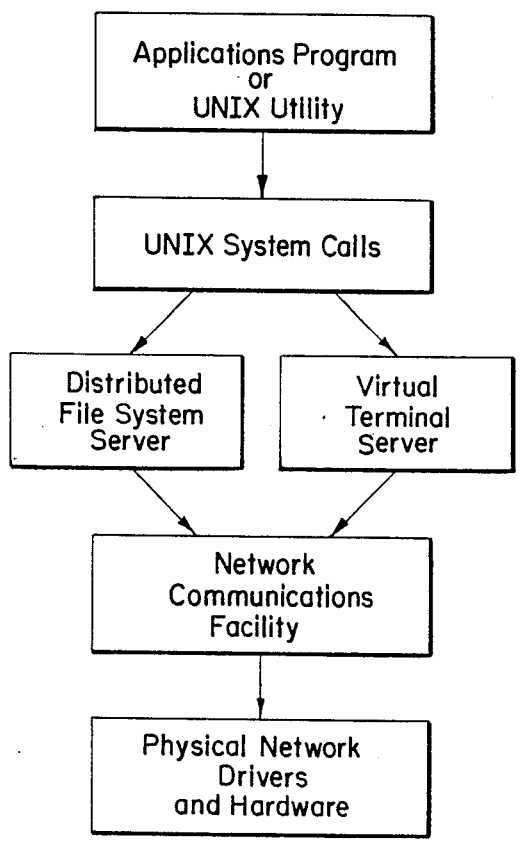
FIG. 14 is a block diagram of an embodiment of a multi-user software operating system which might be utilized in accordance with the principles of the present invention.

As illustrated in FIGS. 13 and 14, the computer system 42 might be an off-the-shelf item such as a 16/32 bit microcomputer designed for the multi-user UNIX operating system. A typical computer system hardware configuration is illustrated in FIG. 13. Multiple communication processors might be utilized to provide sufficient throughput during the communication periods. Communication inputs and outputs might be via RS232 ports. Direct communication with the hospital's mainframe computer might be through a synchronous remote job entry facility with interactive emulation of a mainframe terminal.

The computer system 42 will collect and coordinate the data received from the various terminals 45 and bar code reading devices 48 and store the data in various patient/item data files for later reference and use.

As illustrated in FIG. 14, a network operating system will preferably be utilized which will allow users to interactively access files through a distributed file system. The network operating system will preferably use high level communication protocols which will be independent of the physical network medium utilized, thereby providing ease in networking to other parts of the hospital system which might have different protocols.

Figure 15:
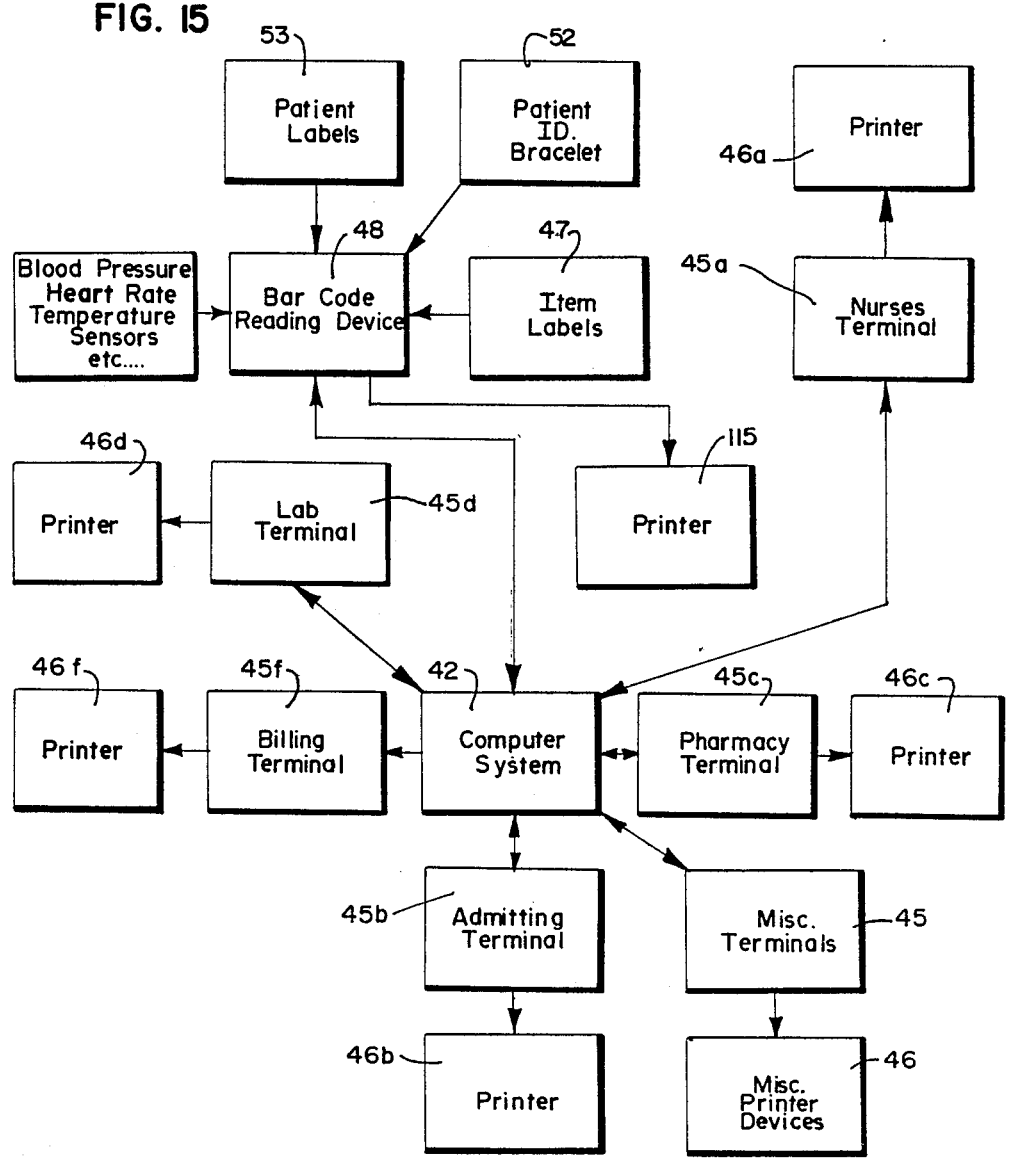
FIG. 15 is a block diagram illustrating a possible arrangement of computer system input/output devices in accordance with the principles of the present invention.

Use of the system and method of the present invention will now be described in terms of a sample scenario and a block diagram which is illustrated in FIG. 15.

At the time of patient admittance, patient information will be entered into the computer system 42 via a terminal 45b at the admitting office. One of the tasks of the admitting staff member will be to print out at a bar code printer 46b a sheet of the bar code labels 53 containing both the patient specific bar code identifiers 51 and the patient's name in human readable form. The bar code labels are placed inside the patient's chart for future use. One of the labels 53 is attached to the patient's medical chart. The patient-unique bar code 50 identifier label will be affixed to the patient's identification bracelet 52 or will be printed on a special patient bracelet by the bar code printer 46b. The bar code identifier 50 on the patient's identification bracelet 52 will be different from that on the labels 53 to enable determination of whether a patient identifying bar code is being read from a patient's identification bracelet 52 or from a label. The bar code 50 for the patient's identification bracelet 52 will be unique from the bar code 51 placed on the labels 53 in the patient's chart to ensure, for example, that it is actually the patient and not the patient's bar code that is receiving drug treatment. Additional patient billing information and other pertinent patient information such as blood type and drugs to which the patient might have an allergic reaction can be entered into the computer system 42 at this time or at some other time when the information becomes available. For example, allergies might be entered at the nurses' terminal 45a after allergy tests have been performed. The patient information will be stored in memory as a suitable patient data file, an embodiment of which is diagrammatically illustrated in FIG. 16. It will be appreciated that any number and configurations of patient data files might be utilized with various types of information. Preferably, duplication of the patient identification bracelet 52 can occur only at the admitting desk.

After a physician writes a prescription prescribing a drug treatment for the patient, a secretary or other staff person will access from a terminal 45a a drug data file stored in the computer system 42 to display at the terminal 45a the list of drugs after scanning the patient identifier bar code 51 on the patient's chart. The staff person will then enter each scanned drug's dosage and frequency of administration via the terminal 45b. Many drugs have a standard dosage and quantity. These standard values can be stored in the appropriate drug data file of the computer system 42 along with the drug such that the dosages, etc. need not be separately entered if the prescription calls for a standard dosage. This enters into the computer system 42 the patient's name, drugs, dosage and times of day they are to be administered. This information is stored in the computer system's memory as a data file correlating the patient and drug information. An example of an embodiment of such a data file layout is diagrammatically illustrated in FIG. 17. It will be appreciated that this data file and/or other data files might include additional drug-related information, such as allergies, etc. The staff person then places a preprinted patient identification bar code label 53 on each of the prescriptions and sends them to the pharmacy for filling.

At the time the pharmacist checks and fills the prescriptions, the pharmacist will scan the patient's identification bar code 51 on the patient's prescription using a bar code reader and will bring up the patient's file at a pharmacy terminal 45c. The pharmacist will check the computer data against the prescription. If the pharmacist does not approve, he will change the prescription or take other appropriate action, such as talking to the responsible doctor. If approved, the pharmacist will then fill the prescription by scanning the drug's identification bar code. He will then scan a bar code in his identification badge indicating his approval. If a bar code identifying the drug is not already on the drug package, the pharmacist will take a pre-coded label and affix it to the drug. This might occur in the case of unit dosages not bar coded by the manufacturer, in which case a sheet of bar codes might be provided which are perforated to the same package size specifications as the package of unit dosages. In the case of unique drugs, such as IV solutions where a pharmacist may combine two or more drugs to form a custom patient IV, a custom bar code might be generated in the pharmacy on its bar code printer 46c and the resulting bar code label affixed to the IV solution. Preferably, the bar code label will list all standard IV information and will also list the names of the ingredient drugs and other pertinent data such as patient's name and rate of delivery (drip rate). If not previously entered, the pharmacist might also manually enter any drug administration guidelines noted by the physician, such as time of day if the drug has no standard times or if the prescription varies from the standard times normally given, although this might be done by the nurse at the nurses' station.

Scanning the drug identifier bar code on the drug package after scanning the patient's bar code will automatically enter and record the drug prescription as being approved for that particular patient and the MAR is updated. Dosage and times per day will be automatically displayed and subsequently printed. However, it will be appreciated that if the times per day for each drug are not stored in the computer system 42, this information can be manually entered at a terminal. Preferably, such things as known allergies for each patient have been previously entered into the patient's computer record such that any drug allergies for a particular patient will be flagged by the computer system and the pharmacist will be informed at the terminal 45c. Moreover, the computer system 42 might be programmed so as to flag any major drug inconsistencies or contradictions at the pharmacy terminal for pharmacy disposition.

In addition, the computer system 42 might also check for significant drug incompatibility problems. If such a problem is detected, a message or alert will appear at the pharmacy terminal 45c.

Moreover, as the prescriptions are filled by the pharmacist or any other item is used or disposed of, the computer system 42 will automatically record such an occurrence in an inventory file identifying all items which have been disposed of, thereby providing for accurate inventory control. An embodiment of such a data file is diagrammatically illustrated in FIG. 18.

Upon approving the prescriptions, a medical administration record (MAR) for that patient is printed at the pharmacy and placed in the patient's drug cart drawer. After all drugs for the period, i.e., eight or twenty-four hours, have been entered and placed in the cart, a patient/drug schedule or assignment sheet might be printed for each nurse, giving names of patients, room numbers and drugs to be dispensed by time of day and dosage for each nurse's shift. Additionally, these records and schedule sheets can be printed at any time at the nurses' stations.

If the pharmacist changes any of the drugs prescribed, such as when filling a prescription with a generic drug, the computer system 42 will mark the new drug. When giving a drug so marked, an alert will be received at the bar code reading device 48 unless the nurses and the pharmacist have both previously entered their personal identifier bar codes to approve the new drug on the MAR. A special flag will be placed on the unapproved MAR to identify a larger than recommended normal dosage. Additionally, a similar alert will be received at the bar code reading device 48 if the dosage prescribed exceeds the maximum dosage specified in the computer system's data files and if the pharmacist and the nurse have not previously entered their personal identifier bar codes.

When ready to administer treatment, a nurse will take the portable RF bar code reading device 48 and read her own identifying bar code badge to access the system and to identify herself. Next, the nurse will read the patient identifier bar code on the patient's identification bracelet and the item identifier bar code on the items to be administered and press a "SEND" key on the bar code reading device 48 while in the patient's room. This activates the transmission of data via the telephone wiring to the computer system 42. While checking a drug against the patient's computer stored data files to verify it properly corresponds to the patient, the bar code reading device 48 will preferably light the amber status light 122b to indicate "in progress" or the words "IN PROGRESS" will be displayed on the liquid crystal display 116 of the bar code reading device 48. In certain instances, it may be necessary for the nurse to use the key pad 114 to enter dosages by use of the "DOS" key, such as in the case of custom made IV solutions or when the dose is other than a unit dose. The bar code reading device 48 might include an optional temperature, pulse and blood pressure cuff module, enabling temperature, pulse and blood pressure data to be directly obtained; however, the nurse can also enter the patient's vital signs via the key pad 114 on the bar code reading device 48. Preferably, the bar code reading device 48 will store and will display upon request six to ten previously entered vital statistics by use of the recall key "REC". This enables a new nurse coming on duty or a physician to access the system when in the patient's room and review on the liquid crystal display 116 the more recent vital signs. Additionally, the bar code reading device will preferably store a record of the most recently administered PRN or other controlled drug administered to control pain or the like and the times they were administered. This eliminates the need to track down the patient's records, which is an important benefit in times of emergency. In addition, scrolling keys might be provided to enable scrolling of the data.

The bar code reading device 48 will preferably include a printer module enabling labels to be printed bedside at a label printer 46e interconnected to the portable bar code reading device 48 such that a nurse can print bar code identifier labels as necessary; for example, a nurse might print a label for attachment to a test tube containing a patient's blood sample by scanning the patient's identification bar code and pressing a print key on the portable bar code reader 48.

If the drug bar code scanned matches the patient identification bar code and the pharmacy-entered drug code, the green status light 122c or other appropriate readout on the LCD 116 will prompt the nurse to proceed. If there is a discrepancy, the red status light 122a might flash and/or some other appropriate readout might appear at the LCD display 116 indicating why the red status light 122a is on. The nurse may elect to override the warning at that time if she believes it is appropriate to administer the drug or take whatever actions she deems necessary. In such cases, a computer record of such events will be stored and will be available for review at a future time.

Preferably, administration of the drug will be automatically recorded when the green status light 122c or other appropriate indication appears on the LCD display 116, or unless the nurse pushes a button on the bar code reading device 48 to indicate that treatment did not occur. If for some reason the nurse cannot proceed with administration of the drug, for example, the patient refusing to take the drug, the nurse will press a "HOLD" key and scan the bar code label on the drug. The patient/drug data files will be updated to reflect that the drug was not taken. The bar code reading device 48 might include several special function buttons on the key pad 114 for explaining why the drug is being held. Although a specific embodiment of the portable bar code reader 48 is illustrated, it will be appreciated that other embodiments might be utilized and that any number and arrangement of special function keys, indicators, input ports, etc. might be present.

Whenever a drug or any other item is dispensed to a patient, the computer system 42 will automatically record such an occurrence in a patient billing file, identifying all items which are to be billed to the patient. An embodiment of such a file is diagrammatically illustrated in FIG. 19. The billing data file is preferably accessible from a terminal 45f in the billing department.

The nurses' terminal 45a will be alerted by the computer system 42 if a drug has not yet been given and is overdue, reminding the station staff to check with the appropriate nurse. Preferably, the computer system 42 will cause a printout of the nurses' drugs and patient's names for the drugs overdue at the terminals associated with printer 46a. Preferably, this will be a buffered output transparent to the printer's normal activity, such that if the printer 46a is in the middle of a printout, the printer will not be interrupted until it is finished. Accordingly, normal printer operation is not interfered with. The computer system data files will include an adjustable time window adjusted and entered by the pharmacist in which the drug can be administered. If drug administration does not occur in this time window, the alert occurs. Moreover, whenever a nurse administers drugs to a particular patient by transmitting via the portable bar code reading device 48 her ID, the patient's ID and the drug's ID, the computer system 42 will check to see if a drug is overdue for any of that nurse's patients. If a drug is overdue, the nurse will be alerted at the portable bar code reading device 48 by the red status light 122a and a message on the display 116.

Preferably a new MAR for each patient and a new assignment sheet for each nurse will be printed at the beginning of each new shift at a printer 46a at the nurses' station. These hard copy reports will provide the nurse coming onto the shift with a record of what has been completed on the previous shift, what has not been completed and what treatment, the time for each treatment and which patient should be treated on the new shift. Additional terminals 46 might be utilized by the nurses to chart additional information before going off their shift.

A permanent MAR may be generated or demanded and placed in the patient's record. The physician can then review this hard copy or go to the nurses' station terminal and review the patient's current MAR on the screen.

The control of controlled drugs such as narcotics is important and regulated in all medical institutions. The present invention performs the following narcotics inventory control functions: (a) reports inventory of all narcotics located or distributed at nursing or pharmacy locations; (b) reports and controls accessibility to such narcotics; and (c) automatically records when supply reaches "reorder" level from main pharmacy. When any narcotics are removed from their locked drawer or drug cart, the nurse scans, in sequence, her badge to identify herself, the cart's own bar code (identifies the stock location) and the narcotic(s) to be administered. The system now has checked the drug out from the cart and has put it into the nurse's inventory, where it will remain until she administers the drug to the patient, via standard procedure as described earlier. If the narcotic(s) are on the patient's electronic MAR, the green status light 122c will be lit. At such time, the narcotics can be administered to the patient in the normal manner. At that time, the narcotic is removed from the nurses' inventory. Dispensing the narcotic to the patient is handled in the same manner as all drugs, except that once the drug is administered to the patient, the narcotic is removed from the "nurse inventory" and automatically billed to the patient. At the end of the shift, a narcotic inventory is printed out, along with who dispensed narcotics, who received narcotics, the nurse(s) leaving the shift, the nurse(s) starting the new shift (who will undertake a physical narcotics count). If any deviations occur, they will have to be corrected via one of the terminals 45. When the inventory level drops to the "automatic order" point, the computer system 42 alerts the pharmacy to fill the drawer. When the drugs are placed in the narcotics cart drawer, the inventory level is again upgraded.

Figures 5, 19, 20:
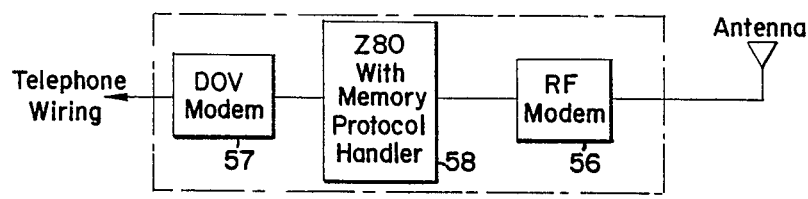
FIG. 5 is a block diagram of an embodiment of the RF/DOV modem illustrated in FIG. 1.
FIG. 19 is a diagrammatic illustration of an embodiment of a patient/item data file.
FIG. 20 is a diagrammatic illustration of an embodiment of a patient/lab test data file.

In ordering a laboratory test, a nurse or other staff person will scan the patient's identification bar code on the patient's chart, and scan or scroll for the bar code for the test required, which might be provided on a preprinted sheet available at the nurses' station. At the lab, a draw list will be printed out at a printer 46d instructing the lab staff which samples to draw from which patients. On each label will be the test's corresponding bar code identifier and name. This label will then be affixed to the test tube or other container required for the test. Before taking the test sample, the lab technician will scan a bar code identifier on his or her badge, scan the patient's identification bar code on the patient's identification bracelet and scan the test bar code on the sample container. The computer system 42 will then indicate if this is the correct patient and the correct test by access to the lab test data file which correlates patients to specific lab tests to be performed. A diagrammatic illustration of such a file is illustrated in FIG. 20. This process will take place in the patient's room. Back in the lab, the technician will scan the patient's identifier bar code on the test sample, perform the test and enter the results into a lab test computer via the terminal 45d or automatically via the test instrument if applicable. The lab test results will be entered into an existing and separate lab test computer system which will perform the usual analysis, although the lab test computer will preferably be interconnected to the computer system 42 for exchange of data and recording of the test results. The lab will be assured that the sample being tested belongs to the correct patient and the results are recorded against the correct patient's data files. In addition, the system will automatically update the billing data file so the patient is billed for the test and will store the dates and times when the test(s) were undertaken for future reference.

The present invention will provide for keeping track of the time a nurse spends with a patient, as well as a time audit record of patient events, such as when a patient is checked in and out, moved to a different area, has tests performed and/or drugs administered, etc. This serves a very useful audit function and drug control function; for example, when a patient is checked out, drugs can be put on hold.

It will be appreciated that the computer system might be programmed in any number of ways to utilize any number and arrangement of data files in providing for identification of patients, relating items to patients and verifying proper correlation between patients and various items.

The present invention will preferably include a data base management capability so that the staff can generate report forms as they wish, in accordance with their procedures.

Alternate Embodiments of the Present Invention

FIGS. 21-35 illustrate alternate embodiments of the present invention. Referring now to FIGS. 21-25, there is illustrated an alternate embodiment of a patient identification and location system and methodology in accordance with the principles of the present invention. An RF transmitter unit 220, reprogrammable to transmit unique patient identifier information, is worn on the body of a patient, preferably mounted in a disposable standard plastic identification bracelet 222 typically worn by a patient in a health care institution and/or badges worn by personnel in the health care institution. In addition, the RF transmitter unit 220 might be mounted on suitable equipment and other moveable items within the health care institution so as to identify and track the items. It will be appreciated that although the present invention has particular application in health care settings, nevertheless, the present invention has application wherever identification and location of personnel and items is required.

Figure 25:
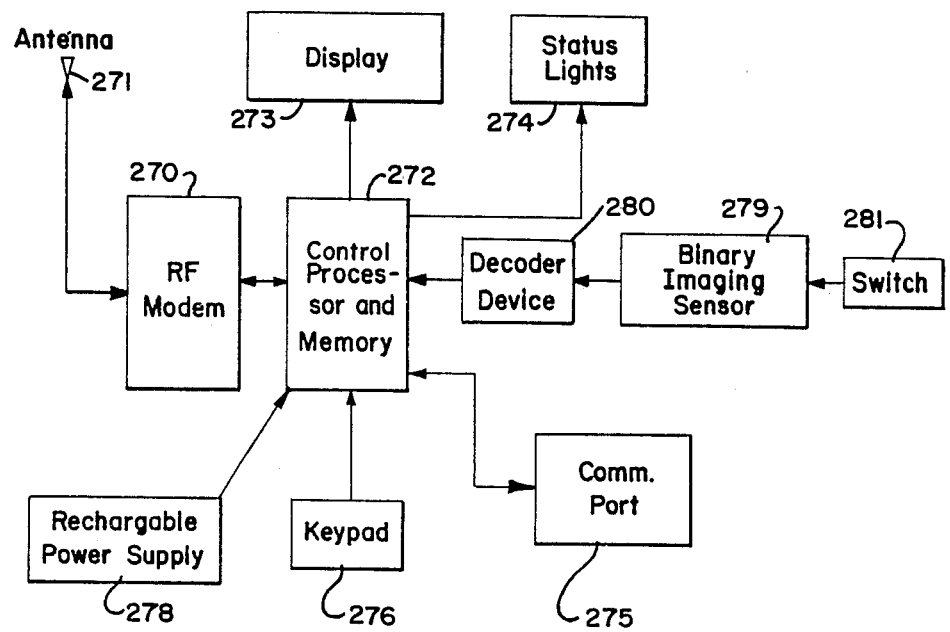

In the embodiment shown, RF signals transmitted by the patient-worn RF transmitter units 220 are received by a plurality of RF receiver units including stationary, known position RF receiver units 226 capable of receiving RF signals strategically located in hallways, dining areas, lounge areas, etc., as well as base stations 228, somewhat similar to the transceiver units 55 of the previous embodiment, which in addition to being capable of receiving RF signals from the transmitter units 220, include a transceiver capability for communication with portable RF transceiver units mounted in portable handheld patient terminals (PHPT) 224, somewhat similar to the bar code reader devices 48 of the previous embodiment, carried by the health care staff and used when administering drugs, taking vital signs, etc. In the embodiment shown, the RF receiver units 226 are not capable of transmitting RF signals, although they too might include a transceiver function. As illustrated in FIG. 25, the portable handheld patient terminals 224 include an RF modem 270 and associated antenna 271, which functions as a transceiver transmitting and receiving RF signals, for retransmittal of the RF signals to the base stations 228 which might be located in the patient's room or other areas wherein patients are frequently present. The base stations 228 include an RF modem and antenna similar to that of the portable handheld patient terminal 224 for receiving and transmitting RF signals to and from the portable handheld patient terminal 224. The base station 228 also receives RF signals directly from the transmitter unit 220. In the preferred embodiment, the portable handheld patient terminal 224 will only communicate with a base station 228 having a corresponding address, the portable handheld terminal 224 and base station 228 being uniquely addressable by storage of an address in memory. The base station 228 will only communicate with a portable handheld terminal 224 having a cooperating address.

Figure 22:
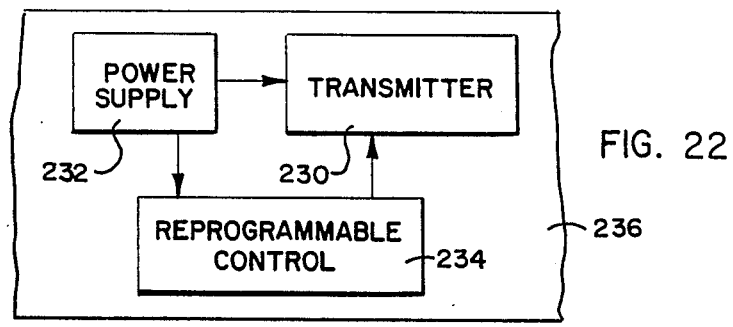

The embodiment of the RF transmitter unit 220 shown in FIG. 22 includes RF transmitter 230, a power supply 232, and reprogrammable control 234 preferably encapsulated in a media 236 so as to be able to withstand sterilization by ethylene oxide or the like; and not be affected by water, body fluids, or common organic solvents and cleaners. The encapsulated RF transmitter unit 220 is suitably removeably mounted on the standard plastic identification bracelet 222 by any number of methods.

The preferred embodiment of the RF transmitter unit 220 can be made to change duty cycles or periodicity of RF transmission by use of proper handshaking signals with the reprogrammable control 234. For example, the RF transmitter unit 220 might typically transmit in a low duty cycle mode of once every two seconds. This transmittal rate is more than adequate for locating a patient. However, when administering drugs, taking vital signs, etc. it is desirable to have a greater frequency of transmission so as to enable more rapid patient identification and better system response time. Thus the portable handheld patient terminal 224 in the preferred embodiment has the ability to change the duty cycle of the RF transmitter unit 220 to a high duty cycle such as twice every second. This might occur when the portable handheld terminal 224 is brought into close proximity with the RF transmitter 220. The RF transmitter unit 220 might have a different range of detection when in the high duty cycle mode. For example, in the low duty cycle, the detection range might be seven meters; while in the high duty cycle, the detection range might be eight to fifteen centimeters. It will be appreciated that the above operating parameters are given by way of example and should not be construed to limit the invention to those specific parameters.

The RF transmitter unit 220 is reprogrammable so as to enable the patient identifier code transmitted by the RF transmitter unit 220 to be changed. The RF transmitter unit 220 is preferably reprogrammable several times throughout its lifetime. For example, if the RF transmitter unit 220 utilizes a microprocessor with a fifteen bit data structure, each RF transmitter unit 220 could be reprogrammed sixty-four times per year and support five hundred beds for a total of 32,768 unique patient identifiers. It will be appreciated that more data bits could be added if needed; but the more bits used the more power consumed, and consequently the shorter the battery life. The power supply 232 will preferably be a battery having a life of one year or more. Examples of such batteries which might be used are lithium, silver oxide, and alkaline. Although not shown, the RF transmitter will preferably include circuitry to shut off the power supply when the RF transmitter unit 220 is not in use.

It is important that the RF signals transmitted by the RF transmitter unit 220 not be affected by static, X-rays, and other electromagnetic fields present in hospital environments.

The RF modem 270 of the portable handheld patient terminal 224 will preferably have a lesser detection range than the fixed position RF receiver units 226, for example, eight to fifteen centimeters, and include a device such as a signal generator to switch the RF transmitter unit duty cycle. Detection might be accomplished by use of a "crystal set" which has a reduced detection range. This eliminates the possibility of the portable handheld patient terminal 224 from being interferred with by other RF transmitter units 220 in the health care facility.

The RF transmitter unit 220 might be built around a three hundred megahertz frequency, although other frequencies might be utilized in order to comply with appropriate governmental regulation. Various types of modulation such as pulse-position modulation (PPM) and frequency-shift keying (FSK) might be used.

Figure 21:
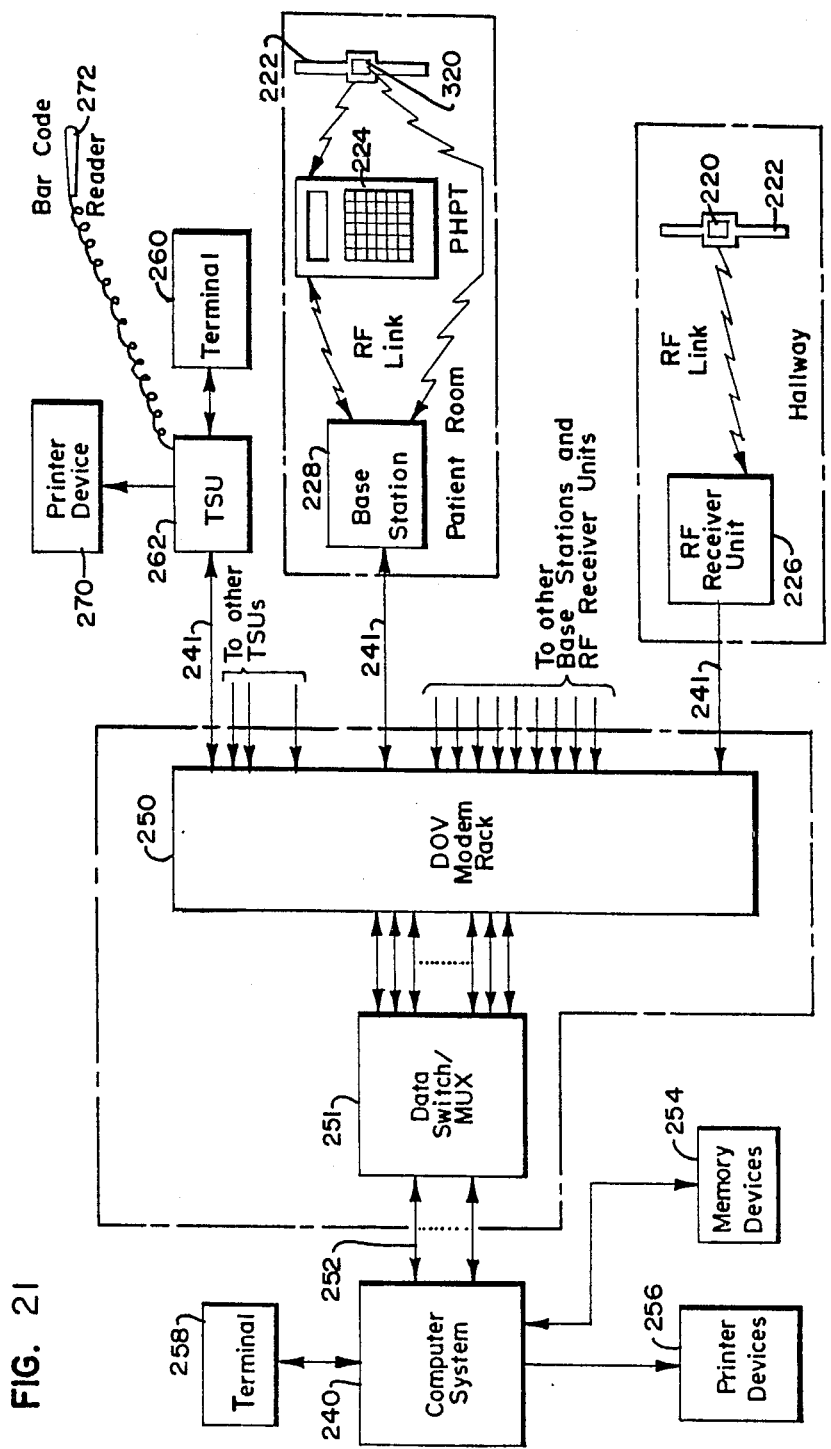

As illustrated in FIG. 21, the fixed position RF receiver units 226,228 are interconnected to a programmed computer system 240 by telephone wiring 241 in a fashion similar to that of the previous embodiment. Upon receipt of a transmission from the transmitter unit 220, the RF receiver units 226,228 will transmit to the computer system 240 by data over voice (DOV) techniques using the telephone wiring 241. In the embodiment illustrated in FIG. 23, the RF receiver units 226,228 include an RF modem 242 for RF reception and a DOV modem 244 for DOV transmission and a microprocessor controlled communication interface 246 which will provide the interface function between the RF modem 242 and the DOV modem 244.

The embodiment of the system illustrated in FIG. 21 includes a DOV modem rack 250 housing a plurality of DOV modems in relatively close proximity to the computer system 240 and includes a corresponding DOV modem 250a for every RF receiver unit DOV modem transmitting to the computer system 240 over the telephone wiring 241. The DOV modems of the modem rack 250 are interconnected to a data switch/multiplexer arrangement 251 for multiplexing the numerous RF receiver DOV modem inputs into the few input/output channels 252 of the computer system 240. The computer system is illustrated as including memory devices 254, printer devices 256, and terminals 258.

The computer system 240 is interconnected to remote dumb terminals 260 distributed throughout the health care facility. The terminals 260 are shown interconnected to the computer system 240 by terminal support unit (TSU) devices 262 via the telephone wiring 241. The TSU 262 includes a DOV modem for communication with the modems of the DOV modem rack 250 so as to enable data over voice (DOV) transmission. The TSUs 262 include ports for interconnection to printers 270 such as bar code printers and dot matrix printers and a bar code reader 272 for reading bar codes. Accordingly, the terminal support unit (TSU) 262 serves as a "data traffic cop" or I/O controller enabling the central computer system 240 to communicate via a single telephone line to the terminal 260, bar code printer, dot matrix printer, bar code reader, etc. The terminal support unit (TSU) 262 provides an interface between the present invention and existing computer systems which might be present in the healthcare facility. In a preferred embodiment, the terminal support unit (TSU) will include four serial ports and one parallel port controlled by a programmed microprocessor and associated memory including read-only memory (ROM).

In some embodiments, the RF receiver units 226, 228 might use twisted pair wiring for communication to the computer system 240. In this embodiment, driver and receiver circuitry might be used to provide RS-232 interface signals. Although not shown, a time division multiplexer might be used to interconnect multiple ones of the RF receiver units 226, 228 to the computer system 240. A limited distance modem is another alternative for transmitting on the twisted pair wiring. Yet another method of communication to the central computer is using power line carrier (PLC) techniques for transmission over the AC wiring.

A user wishing to locate an object, e.g., a patient, can use the terminals 258, 260 to enter the patient's name or unique identifier. This will activate the computer system program which will then display at the terminal the location of the RF receiver unit 226, 228 wherein the patient was last detected. An example display on the terminal, might display patient name/identifier, location, e.g., dining room, and time at location. In addition, the terminal might display or a hard copy printout be made of the patient's movements over a user selected period of time and at a user selected time interval.

Figure 24:
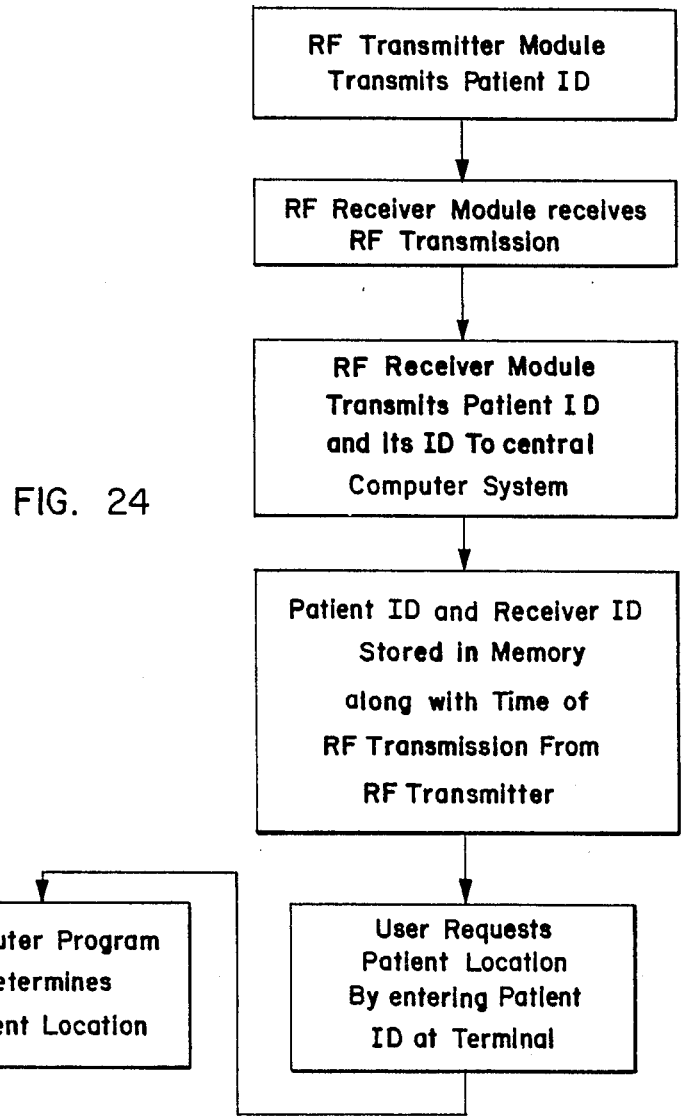
Figure 23:
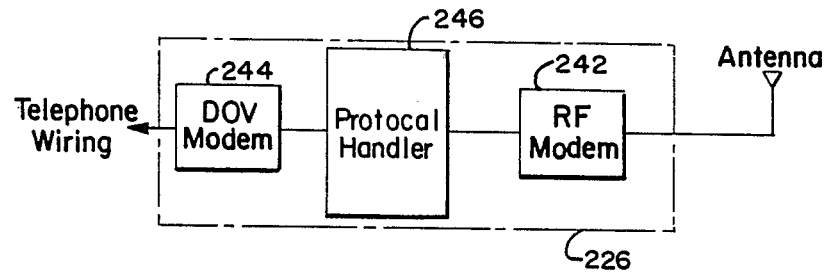

Illustrated in FIG. 24 is an embodiment of a method in accordance with the principles of the present invention. The RF transmitter units 220 will periodically transmit unique object identifier information identifying the object wearing the transmitter. The RF transmissions will be detected by one or more of the RF receiver units 226,228. The RF receiver units 226,228 transmit the unique object identifier information to the computer system 240 as well as identifier information identifying the RF receiver unit 226,228 sending the object information. The object and RF identifier information will be stored in appropriate data files contained in computer system memory. Also, the time and date of the RF transmitter unit 220 transmission to the RF receiver unit 226,228 will be store in an appropriate data file. The time might be determined by the computer system noting when an input from the RF receiver units 226,228 is received although other methods can be used. Upon request by a user at one of the terminals, the computer system program will transmit the location of the object to the user terminal. In the preferred embodiment, the object's location will be determined by the location of the RF receiver unit 226,228 to last detect the object's transmitter, the location of the RF receiver units 226,228 being known and stored in the memory of the computer system. In addition, the preferred embodiment of the invention can be used to maintain a time record of staff and patient activity. This is particularly helpful in determining how long a particular activity takes. Moreover, an historical record of staff and patient movements over a specified period of time, e.g., days, at selected intervals can be requested.

Illustrated in FIG. 25 is an embodiment of a portable handheld patient terminal 224. As illustrated, the portable handheld patient terminal 224 is controlled by a microprocessor and memory 272. The portable handheld patient terminal 224 might include a liquid crystal display 273, various status lights 274 indicating different conditions of operation, a communications port 275 for input and output of data, a keypad 276 for entry of data, and a rechargeable power supply 278. In addition, as illustrated, the portable handheld patient terminal might include a binary imaging sensor with associated decoder device 280 for reading bar codes and other alphanumeric indicia. A switch 281 is illustrated as controlling operation of the binary imaging sensor.

In addition to locating objects, the present invention can be used to identify patients, staff, drugs, supplies, etc. when administering drugs, taking vital signs, etc. The RF transmitter units 220 might be the primary means of identification or a secondary means for providing a second means of patient identification verification or backup.

Although wireless electromagnetic transmissions in the radio frequency (RF) range have been discussed in the preferred embodiment, alternate types of wireless electromagnetic transmissions might be utilized, e.g., infrared.

Referring now to FIGS. 26-35, there is illustrated an alternate embodiment of the bar code reader devices 48 and the portable handheld patient terminals 224, herein referred to as a portable handheld terminal 320. As illustrated in FIG. 26, the portable handheld terminal 320 is packaged in a portable handheld housing 322 having first and second spaced apart, opposing major surfaces 324,326, respectively, extending generally along the longitudinal axis of the portable handheld terminal 320 between first and second end portions 328 and 330, respectively. The first major surface 324 might also be referred to as the bottom surface, and the second major surface 326 might also be referred to as the top surface. The first end portion 328 might also be referred to as the front end portion, and the second end portion 330 might also be referred to as the back end portion. As illustrated, interconnected to the housing 322 proximate the first end portion 328 is an elongated handle portion 340 which extends upwardly away from the second major surface 326 and backwardly generally along the longitudinal axis of the housing 322 toward the second end portion 330. As illustrated, in the embodiment shown, the handle portion 340 includes an arcuate portion 342 and a substantially straight portion 344 which is spaced sufficiently far from the second surface 326 of the portable handheld terminal 320 so as to enable a user's hand 350 to grasp around the handle portion 340 with the user's fingers extending into the space between the handle portion 340 and the second major surface 326 as illustrated in FIG. 26. The handle portion 340 enables the terminal to be held in either hand during use. In an alternate embodiment, the handle portion 340 might be interconnected to the housing at both ends. The portable handheld terminal will preferably be made by conventional molded plastic processes.

As illustrated in FIG. 28, when seen from the back end portion 330, the portable handheld terminal 320 has a generally truncated pyramid shape, generally becoming narrower toward the top.

Figure 30:
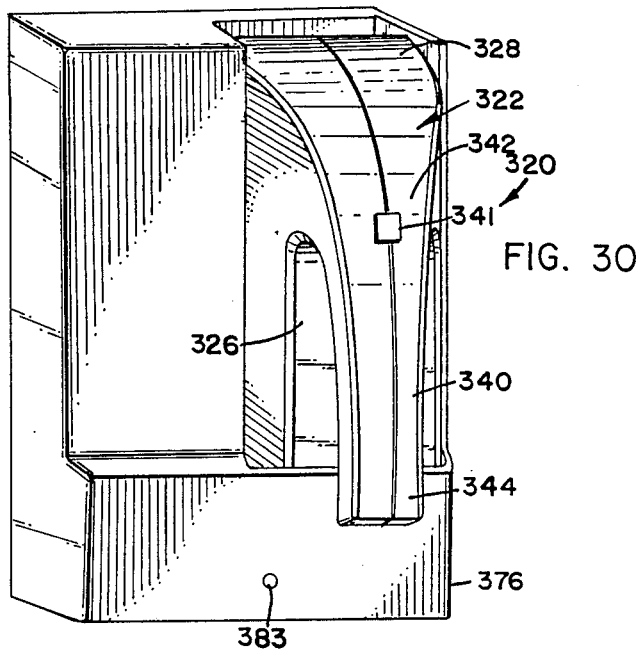
Figure 35:
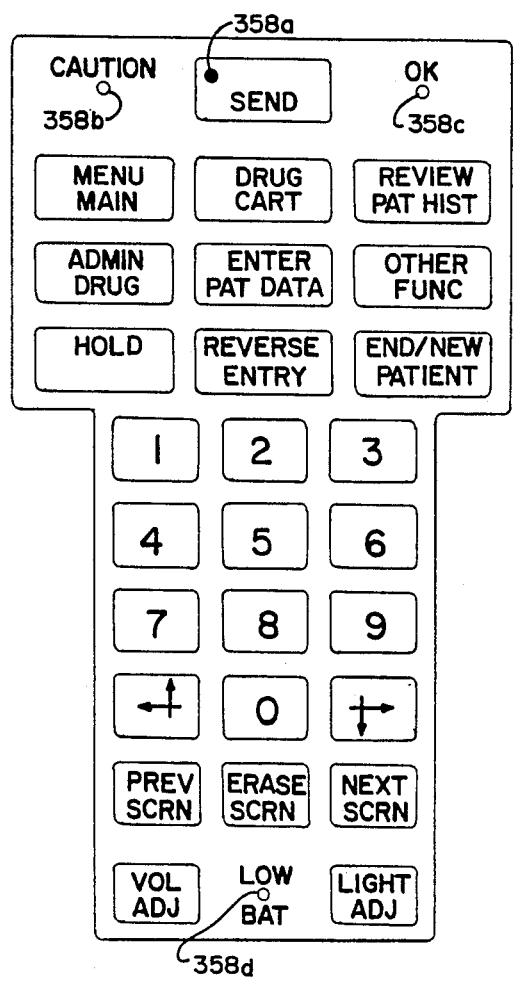

As illustrated in phantom line in the embodiment shown in FIG. 27, located proximate the first end portion 328 of the portable handheld terminal 320 is an optical sensor device 352 of a bar code reader. As illustrated in FIG. 30, positioned on the handle 340 is a push button, contact switch 341 for activating the sensor device 352 via an appropriate electrical interconnection. The switch 341 will normally be in an off position and will return to the off position upon being released by the user. Disposed on the first major surface 324 is a liquid crystal display (LCD) 354 which in the embodiment shown is capable of displaying four lines of text, each line containing up to twenty characters. Also disposed on the first major surface 324 is a keyboard 356. In the preferred embodiment, a membrane keypad is used. An embodiment of the keyboard is illustrated in FIG. 35. In the embodiment shown, the keyboard 356 includes status lights 358, special function keys 360, and a numeric keypad 362.

Figure 29:
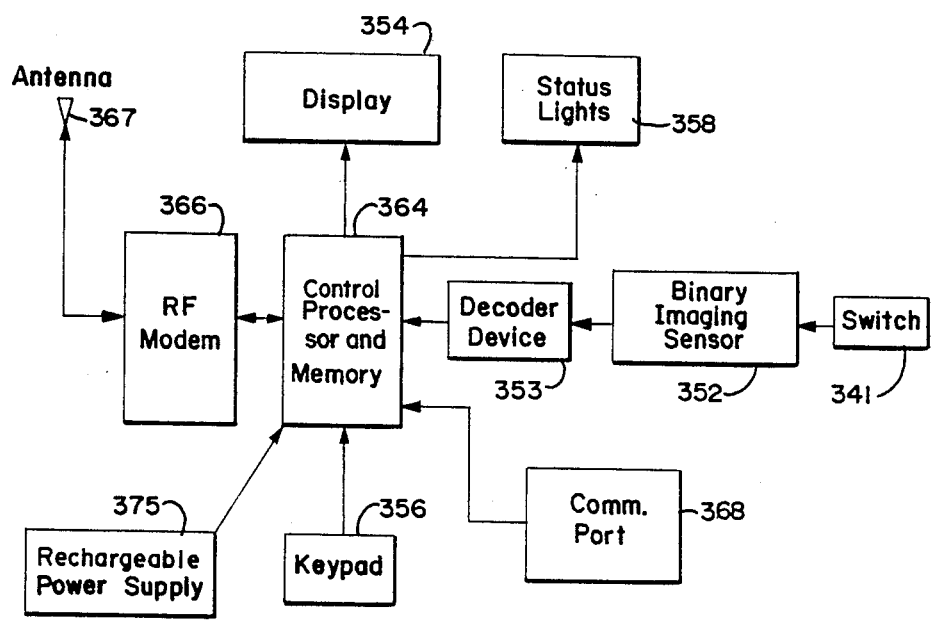

As illustrated in the block diagram shown in FIG. 29, the portable handheld terminal 320 includes a microprocessor and associated memory 364. An example of one such microprocessor is an INTEL 3031. In addition, the portable handheld terminal includes an RF transceiver arrangement including an RF modem 366 and antenna 367 for real time data transmission and reception of RF signals. Moreover, a communications port 368 including a multipin connector is present for input of data to and output of data from the portable handheld terminal 320. The portable handheld terminal 320 is provided with additional memory so as to enable storage of data and downloading at a later time via the communications port 368. For example, the portable handheld terminal 320 might store vital signs, drugs administered, etc. for a plurality of patients. In addition, external vital signs measurement equipment might be interconnected to the communications port 368 for input of data. The communications port 368 includes a multipin connector. In addition to input and output of data, the communications port 368 will also be used in the preferred embodiment for charging a rechargeable, removable power supply 375 of the portable handheld terminal 320. In the preferred embodiment, the portable handheld terminal 320 will operate for over one hour between recharging.

The optical sensor device 352 is preferably a binary imaging device such as a charged coupled device or optic RAM device; e.g., Hitachi Model No. HE97134. The optical sensor device 352 includes an optical lens and a low-powered, high sensitivity light source 355 for illumination of the bar code indicia. The optical sensor device 352 includes an image capture device including an X-Y array of light sensitive elements; e.g., a 2048 pixel array of light sensitive elements, which will provide a digital image of the bar code indicia being read. Accordingly, the present invention will simply require the user to point the optical sensor device 352 of the portable handheld patient terminal 320 at the bar code indicia and press the switch 341 on the handle portion 340 to take an electronic digital "picture" of the bar code indicia. The electronic digital "picture" is then electronically interpreted by a microprocessor controlled decoder device 353. It will be appreciated that charged coupled devices and optic RAM devices are commercially available.

As illustrated in FIGS. 30-34, the portable handheld terminal 320 is used in conjunction with a wall mounted base station 376 for wireless communication with the portable handheld terminal and for storage of the portable handheld terminal 320 during non-use. The base station in the embodiment shown, includes an RF transceiver arrangement including an RF modem 379 and antenna 380 for communicating with the RF transceiver arrangement of the portable handheld terminal 320. The base station 376 further includes a data over voice (DOV) modem 377 for data over voice communications over telephone wire to a computer system. In addition, the base station 376 will include a central processor and memory 373 for controlling operation of the base station 376 and in particular handling the communication interface between the DOV modem 377 and the RF modem 379, as well as communication with the computer system. The base station 376 preferably derives its power from a transformer 381 interconnected to an AC power supply. In addition, the base station 376 includes a communications port 382 adapted for interconnection to the communications port 368 of the portable handheld terminal 320.

The base station 376 includes non-volatile memory 386 which can be programmed to uniquely address the base station 376. When the portable handheld terminal 320 is stored at the base station 376, the base station 376 will download its unique address or identifier via the communications ports 382,368 into the memory of the portable handheld terminal. When transmitting to the base station 376, the portable handheld terminal 320 will include this address or identifier with its transmissions. If the identifier is not recognized by the base station 376, the base station will ignore the transmission and not respond. This prevents interference with the base station 376 by other portable handheld terminals 320 located throughout the facility. In a preferred embodiment, the portable handheld terminal is capable of programming the address or identifier of the base station 376. This is accomplished by the operator entering an appropriate command at the keyboard of the portable handheld terminal which is recognized by the base station and indicates to the base station that its address is to be modified by the portable handheld terminal 320. When the portable handheld terminal 320 is stored in the base station 376, the unique address or identifier will be downloaded from the portable handheld terminal to the non-volatile memory 386 of the base station.

Figure 33:
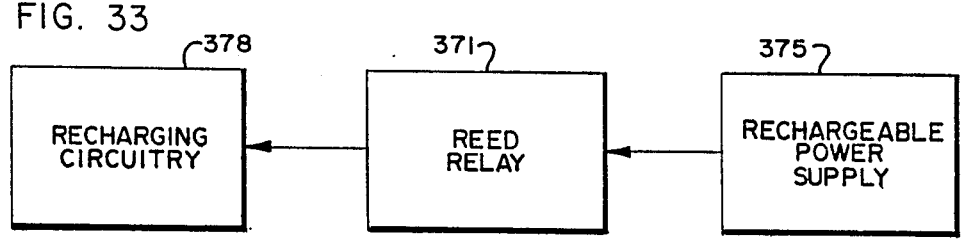
Figure 34:
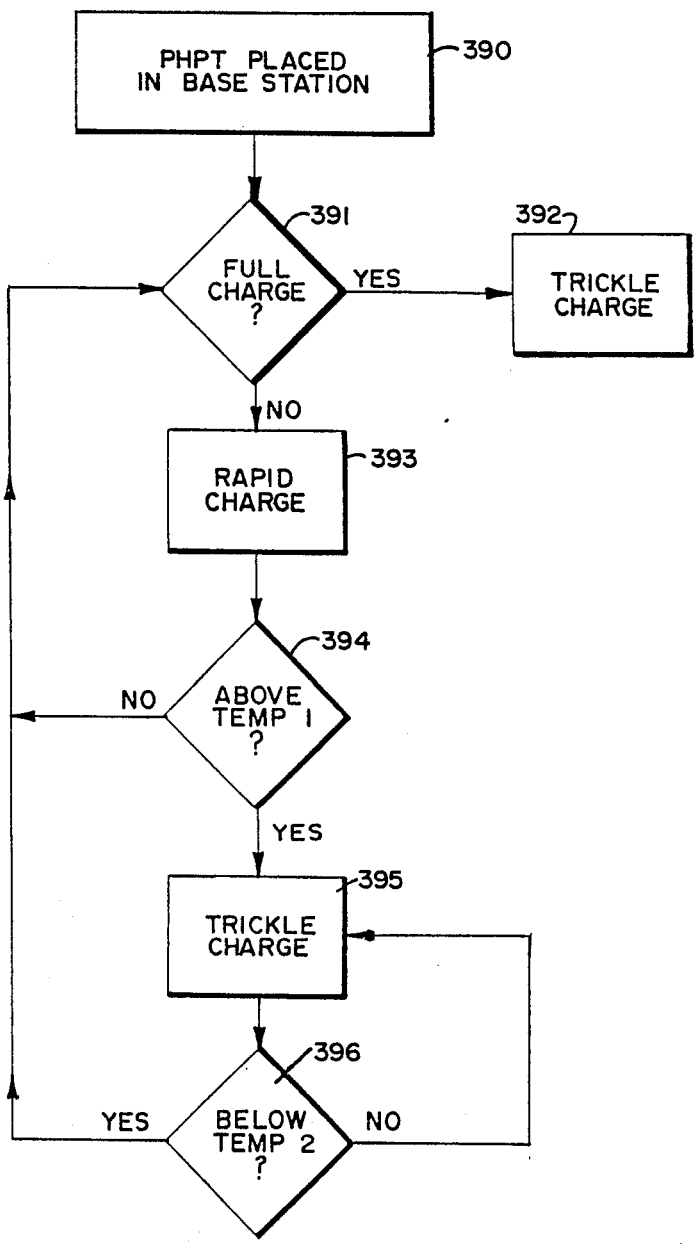

As illustrated, the base station 376 includes recharging circuitry 378 for charging the rechargeable power supply 375 of the portable handheld terminal 320. As illustrated in FIG. 33, the recharging circuitry 378 is interconnected by a temperature sensor, a read relay 371, mounted to a battery cell in the rechargeable power supply 375 of the portable handheld terminal 320. The read relay 371 is mounted so as to provide sensing of the highest temperature in the battery pack. The relay 371 will have one lead connected to the positive terminal of the battery pack and the other lead provided to the recharging circuitry 378 through the communication ports 368,382. In operation, as illustrated in FIG. 34, when the portable handheld terminal is placed in the base station as illustrated at block 390, the base station 376 will check to see if the power supply 375 is at full charge as illustrated at decision block 391. If the power supply is at full charge, the recharging circuitry 378 will switch to a trickle charge mode as illustrated at block 392. In the trickle charge mode, the recharging circuitry 378 will provide power to the logic control of the portable handheld unit. As illustrated at block 393, if the power supply 375 is not fully charged, the recharging circuitry 378 will provide a rapid charge. In the preferred embodiment, rapid charge current is at 2C=900 mA while trickle charge is at C/3=150 mA. The recharging circuitry 378 will check to see if the power supply 375 has reached a critical temperature (Temp1) as illustrated at block 394. If the critical temperature has been reached, then, as illustrated at block 395, the recharging circuitry 378 will switch into trickle charge mode. The recharging circuitry 378 will monitor the temperature such that if the temperature falls below a specified temperature (Temp2) as illustrated at block 396, the recharging circuitry 378 will go back to rapid charge mode if the power supply is not fully charged.

Mounted on the outside of the base station 376 is a status light 383 which varies in intensity between trickle charge and rapid charge so as to indicate the charging mode. The status light 383 will come on as soon as the portable handheld terminal 320 is properly inserted in the base station 376.

The power supply 381 will preferably provide the following power outputs:

400 mA at +5.0 V
80 mA at +7.2 V
100 mA at +12 V
100 mA at −12 V

Figure 32:
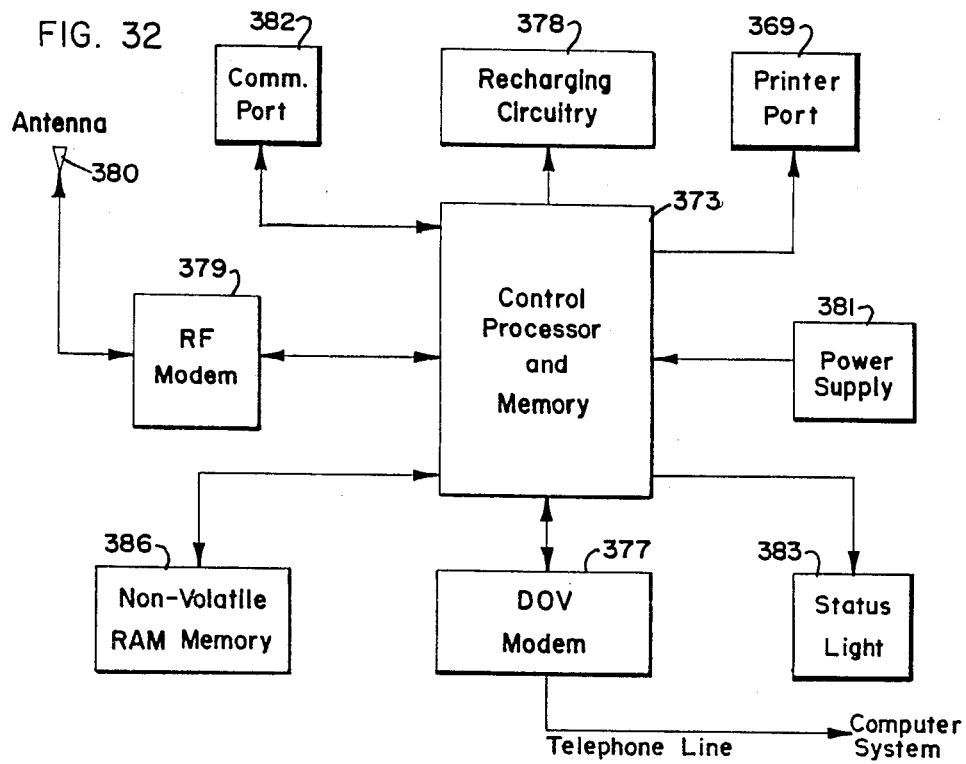

In addition, as illustrated in FIG. 32, the base station 376 might include a communications port 369 for interconnection to a printer.

The power supply 375 in the portable handheld terminal might include removable batteries or a removable battery pack stored in the handle portion 340 or between the surfaces 324,326 proximate the end portion 330.

As previously indicated, electrical interconnection between the portable handheld terminal 320 and the base station 376 will be provided by the communications ports 368,382 which might comprise a standard multipin type of interface connector. In addition to use for recharging and addressing of the portable handheld terminal 320, the communication ports might be utilized for diagnostic testing of the portable handheld terminal 320.

Figure 31:
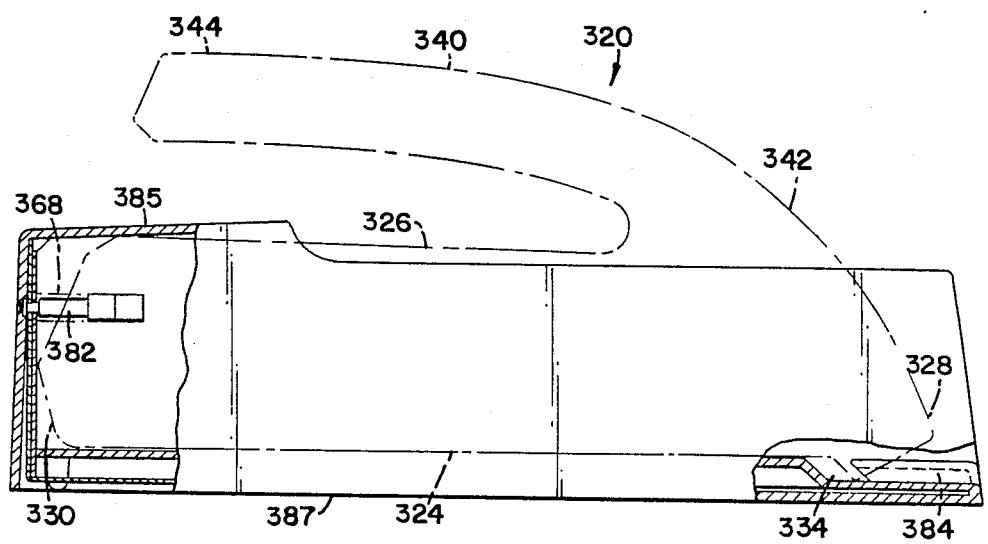

Although not shown, the base station 376 might include a biasing mechanism for forcing the portable handheld terminal 320 in a generally upward direction such that an edge 384 of the base station 376 cooperates with an inside wall 334 of the portable handheld terminal housing portion defining a window or opening 335 for an optical sensor 352. As illustrated in FIG. 31, a wall 385 of the base station 376 might cooperate with a back wall 387 to define a cavity for receipt and retention of the back end portion 330 of the portable handheld terminal 320. The wall 385 slants at a slight angle away from the wall 387 so that the portable handheld terminal 320 can be inserted downwardly with low insertion force into proper connection with the multiple pin connector of the communications port 382 and tilted outwardly to enable easy mounting and removal thereof from the base station 376. The mating connector arrangements of the communication ports 368,382 are capable of being connected numerous times.

The base station 376, in addition to communicating over existing telephone wiring, might communicate via twisted pair wiring in a serial interface fashion, as part of a local area network, or over the existing AC wiring using power line carrier (PLC) techniques, etc.

In typical use, the user will enter data at the handheld portable terminal 320 via the keyboard 356 and the optical bar code reader 352 and transmit the same as RF signals to the base station 376. The base station 376 will then communicate with the central computer system wherein master data files might be kept. The central computer system will, upon receiving the data, respond and provide output data to the base station 376 which will, in turn, communicate by RF signals to the portable handheld terminal 320.

It will be appreciated that other forms of electromagnetic transmissions might be utilized other than radio frequency (RF) transmissions, e.g., infrared.

The keypad of the portable handheld patient terminal 320 will allow the operator to select the function desired, allow manual entry of information, and control the operation of the handheld terminal. An audible alarm sounds if an invalid key is pressed. Also, an indication will be displaced at the LCD indicating that an invalid key was pressed. This screen will be shown for a period of time and then the portable handheld patient terminal will display the screen that was shown before the invalid key was pressed. During communications with the base station 376, the keys on the portable handheld patient terminal 320 will not function.

Access to any function via the keyboard can only be accomplished by reading of a hospital staff ID badge after the portable handheld patient terminal 320 is removed from the base station 376 or after the "new patient" key is depressed. The liquid crystal display will display to the user an indication to scan their ID badge. After a valid scan of their ID badge, the portable handheld patient terminal will be in the main menu for function selection. Access to the system has now been gained. Once access is gained, the ID number of the staff person is retained until access to functions is cancelled. When a function requiring patient ID or drug cart ID is requested, the portable handheld patient terminal 320 will prompt the user to scan the appropriate bar code, if it has not already been entered. The patient ID or drug cart ID can be entered before the function selection is made. Once entered, all IDs are retained until access to functions is cancelled. Access to functions is done whenever the functions for a particular patient or drug cart are complete. This is accomplished by depressing the "end/new patient" key or placing the portable handheld patient terminal into the base station 376. In a preferred embodiment, the access to functions is cancelled thirty seconds after the portable handheld patient terminal is placed into the base station. Once this is done, the portable handheld patient terminal goes into an inoperative mode except for diagnostics which might be initiated by the computer system. Even though the portable handheld patient terminal has not been placed back in the base station, if there have been no valid functions performed for a period of five minutes, access to the system functions via the portable handheld patient terminal is cancelled. This is to avoid unauthorized personnel access if the staff personnel forget to press the "end/new patient" key. The staff ID, drug cart ID, and patient ID will be removed from the memory of the portable handheld patient terminal when access to functions is cancelled. If a function is in process when the "end/new patient" key is pressed, an audible alarm will sound. The portable handheld patient terminal can only be turned off by pressing the "end/new patient" key when in the main menu. Data design to be entered via bar codes, e.g., staff ID numbers, patient ID numbers, supplies identification, drug identification, drug cart identification, etc. cannot be entered via the keypad 356. Patient data such as vital signs, patient assessments, etc. can be entered via the keypad, as well as quantity items.

The following is a brief description of the various keys of the keypad 56:

| KEY | DESCRIPTION |
| --- | --- |
| MAIN MENU | The "MAIN MENU" key can be used any time after a function has been selected. The portable handheld patient terminal 320 will be in the mode as when it was first accessed. Staff ID, cart ID, and patient ID |

| KEY | DESCRIPTION |
|---|---|
| | will be retained in the portable handheld patient terminal 320. When the "MAIN MENU" key is pressed, the LCD display will display a message to the operator. It will indicate that any data entered for the function they are in will be lost if it is not sent to the base station 376 and thence to the computer system before the "MAIN MENU" function is carried out. It will allow the operator to either go back to the function they were in, or go ahead with the "MAIN MENU" selection. |
| END/NEW PATIENT | The "END/NEW PATIENT" key will cancel access to functions. |
| ERASE SCRN | The "ERASE SCRN" key will erase all the data which had been entered, either manually, automatically, or with the bar code reader, that is presently shown on the LCD display. |
| SEND | The "SEND" key is used in conjunction with the other keys to perform a function. When the send key is pressed, data about the function desired to be performed is sent to the computer system via the base station 376. If the "SEND" key is accepted for input, a yellow LED 358a on the "SEND" key is lit. The use of the portable handheld patient terminal when the RF transceiver is inoperable is possible. This would be done by returning the portable handheld patient terminal 320 to the base station 376 after the "COMMUNICATIONS ERROR" message has been displayed on the LCD display 354. The amount of time between when the "COMMUNICATIONS ERROR" message has been displayed on the LCD display 354 and when the portable handheld patient terminal 320 is returned to the base station 376 is limited to 30 seconds. When a response is received from the host computer system, the time out feature is started again. The audible alarm will indicate to the operator that the communications to the host computer system is complete. If the portable handheld patient terminal is to be used again, such as for another function or to correct a red light condition, the timeout will be 30 seconds. The portable handheld patient terminal will have to be removed from the base before this happens. |
| HOLD | The "HOLD" key can only be used in specified functions. It will give the staff member the ability to hold a test order, surgical order, or a drug administration. The hold feature will give the option of: Delaying the time for the procedure/administration and the associated warnings that are given when they are late. This delay is determined by the application software of the host computer system. Not giving a particular order/prescription for one administration from the MAR. This is done if it is determined that the |
| | procedure/administration will not be done at a later time. |
| REVERSE ENTRY | The "REVERSE ENTRY" key can only be used in specified functions. It will give the staff member the ability to undo a function which was previously recorded, (sent to the host computer system) in the host computer system such as: When a drug had been recorded as administered to a patient, but is not given. When test samples had been recorded as taken from a patient, but are not. When supplies had been recorded as used by a patient, but are not. When controlled drugs have been recorded for cart replenishment, but are not delivered. When controlled drugs checked out by a staff member need to be returned to the drug cart. The "REVERSE ENTRY" key will place a minus (−) in front of the quantity field on the LCD display. |
| PREV SCRN | The "PREV SCRN" key can be used in functions which contain more than one screen of information. This key will allow the operator to view screens of information entered prior to the screen presently displayed. This feature will be useful in reviewing patient vital signs and patient assessments which were recalled from memory, as well as reviewing data entered before it is sent. |
| NEXT SCRN | The "NEXT SCRN" key can be used in functions which contain more than one screen of information. This key will allow the operator to view screens of information entered after the screen presently displayed. This feature will be useful in reviewing patient vital signs and patient assessments which were recalled from memory, as well as reviewing data entered before it is sent. |
| (RIGHT ARROW) | The "(RIGHT ARROW)" key is used to move the cursor on the LCD display to the various fields for data entry. By pressing this key, the cursor will move to the first character location in the next field to the right, on the same line. If there are no more fields on the same line, the cursor will move to the left most field on the next line. If the cursor is in the last field on the last line, it will wrap around to the first field on the first line. If there is already data in a field, entering any bar code or numeric key when the cursor is at the first character will erase the previous data and allow for the new data to be entered. |
| (LEFT ARROW) | The "(LEFT ARROW)" key is used to move the cursor on the LCD display to the various fields for data entry. By pressing this key, the cursor will move to the first character location in the next field to the left, on the same line. If there are no more fields on the same line, the cursor will move to the right most field on the previous |

| KEY | DESCRIPTION |
|---|---|
| | line. If the cursor is in the first field on the first line, it will wrap around to the last field on the last line. If there is already data in a field, entering any bar code or numeric key when the cursor is at the first character will erase the previous data and allow for the new data to be entered. While entering data in a field, pressing the left arrow key will provide for editing of the data. It will function as a backspace key, and the characters will be erased from the field as the key is pressed. If all characters in a field are erased by using the left arrow as a backspace, the cursor jumps to the first character in the previous field. |
| ENTER PAT DATA | The "ENTER PAT DATA" is used to enter patient vital signs and patient assessment. In the preferred embodiment, the formatted display will be presented at the liquid crystal display for entry of the vital signs and patient assessment. |
| REVIEW PAT HIST | The "REVIEW PAT HIST" key is used to review patient vital signs and administrations. |
| DRUG CART | The "DRUG CART" key is used to replenish and check out controlled drugs from the drug cart, and verify the drug cart inventory of controlled drugs. |
| ADMIN DRUG | The "ADMIN DRUG" key is used for patient and drug verification for drug administration. |
| OTHER FUNC | The "OTHER FUNC" key is used for patient and sample verification for taking of samples, billing for patient use of supplies, checking a patient into a new location, and displaying other functions which might be available on the system. |

There are four LED indicators on the portable handheld patient terminal 320. The liquid crystal display (LCD) 354 will also provide information relating to the LEDs. The yellow LED 358a will be lit when the SEND key is pressed and will remain lit until communications with the base unit is complete. During this time, the user cannot make any entries at the keyboard. A red LED 358b is lit when information entered for a function desired does not match what is the correct information for that function, or when an invalid key is pressed. The red LED 358b is a warning not to proceed without first checking for a potential problem. The red LED will remain lit continuously under the first condition until some action is taken to remedy the problem. Under the second condition, the red LED will remain lit while the LCD displays the invalid key pressed message. A green LED 358c is lit when a function is valid to proceed. The green LED is lit momentarily under this condition. The green LED is also lit when the central computer system acknowledges receipt of proper information. The green LED is lit continuously under this condition until some other action is taken. A yellow LED 358d will indicate the early warning of a low battery in the portable handheld patient terminal. This is an early warning level and the portable handheld patient terminal will still function. However, operation of the portable handheld patient terminal will be locked out when the batteries reach a level where the data in the patient history is corrupted. Before lock out occurs, the LCD display 354 will display a warning.

Preferably, the LCD display 354 will be capable of displaying four lines of text each containing twenty characters. The LCD will have a lighting source which will provide illumination under low light conditions. This lighting will be controlled by a key on the keypad switching the lighting source from the on to off or off to on condition.

It is to be understood, however, that even though numerous characteristics and advantages of the present invention have been set forth in the foregoing description, together with details of the structure and function of the invention, the disclosure is illustrative only, and changes may be made in detail especially in matters of shape, size and arrangement of parts within the principles of the present invention to the full extent indicated by the broad general meaning of the terms in which the appended claims are expressed.

What is claimed is:

1. A patient identification and verification system comprising:

(a) programmed system computer means for processing and storing patient data;

(b) input means operatively interconnected to the programmed system computer means for input of data to the programmed system computer means;

(c) output means operatively interconnected to the programmed system computer means for output of data from the programmed system computer means;

(d) first bar code identifier means adapted for attachment to a patient for identification of the patient, the bar code identifier means including a patient unique code;

(e) a plurality of second bar code identifier means for identifying patient care related items, such as medication, etc.;

(f) the input means and output means including:

(i) microprocessor controlled portable handheld patient terminal means having bar code reader means for scanning the first bar code identifier means to identify the patient and for scanning the second bar code identifier means for relating various items to a specific patient, the portable handheld patient terminal means further including keyboard means for data entry and display means for display of information, the portable handheld patient terminal means including electromagnetic wave transceiver means including means for transmission of patient and item data as an electromagnetic wave which is representative of the first and second bar code identifier means scanned by the bar code reader means and including means for receipt of data as an electromagnetic wave;

(ii) microprocessor controlled base station means including electromagnetic wave transceiver means for receipt of and transmission of the patient and item data as an electromagnetic wave to the electromagnetic wave transceiver means of the portable handheld patient terminal means, the base station means being interconnected to the programmed system computer means at least in part by electrical lines for receipt and transmission of the patient and item data on the electrical lines to the programmed system computer means, the base station means includes a programmable unique identifier, the base station means including means for only allowing communication with a portable handheld patent terminal means having a corresponding program identifier, the patient system including means for programming the portable handheld patient terminal means with the corresponding identifier; and (iii) the programmed system computer means including program means for verifying the patient and item data properly correspond and transmitting an alarm signal if improper correspondence noted.

2. A system in accordance with claim 1, wherein the programmed system computer means includes output means for output of an alert at a remote printer device indicating administration of a medication for a particular patient is overdue, the output means operating in a mode transparent to that of the printer device's normal operation, such that the printer's normal operation is not interrupted.

3. A system in accordance with claim 1, wherein the electrical lines interconnecting the base station means to the programmed system computer means comprise previously existing telephone lines.

4. A system in accordance with claim 1 wherein the base station means includes program means for programming the portable handheld patient terminal means with the corresponding identifier.

* * * * *

UNITED STATES PATENT AND TRADEMARK OFFICE
CERTIFICATE OF CORRECTION

PATENT NO. : 4,857,716
DATED : August 15, 1989
INVENTOR(S) : Gombrich et al.

It is certified that error appears in the above-identified patent and that said Letters Patent is hereby corrected as shown below:

Title page:

Abstract, line 13, "codes" should be --code--.

Col. 1, line 42, after "bracelet" insert a period.

Col. 4, line 31, "t" should be --to--.

Col. 6, line 16, "system" should be --systems--.

Col. 6, line 33, "FIG." should be --FIGS.--.

Col. 6, line 68, "rechargable" should be --rechargeable--.

Col. 21, line 38, "store" should be --stored--.

Col. 29, line 15, "functicn" should be --function--.

Col. 31, line 5, "patent" should be --patient--.

Signed and Sealed this

Fifth Day of February, 1991

*Attest:*

HARRY F. MANBECK, JR.

*Attesting Officer*  Commissioner of Patents and Trademarks